(12) United States Patent
Fukuda

(10) Patent No.: US 10,335,107 B2
(45) Date of Patent: Jul. 2, 2019

(54) TOMOGRAPHIC IMAGE GENERATION DEVICE AND METHOD, AND RECORDING MEDIUM

(71) Applicant: FUJIFILM Corporation, Tokyo (JP)

(72) Inventor: Wataru Fukuda, Ashigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 881 days.

(21) Appl. No.: 14/854,762

(22) Filed: Sep. 15, 2015

(65) Prior Publication Data

US 2016/0081644 A1 Mar. 24, 2016

(30) Foreign Application Priority Data

Sep. 19, 2014 (JP) .................................. 2014-190784
Aug. 20, 2015 (JP) .................................. 2015-162559

(51) Int. Cl.
 *A61B 6/02* (2006.01)
 *A61B 6/00* (2006.01)
 *G06T 11/00* (2006.01)

(52) U.S. Cl.
 CPC ............ *A61B 6/5205* (2013.01); *A61B 6/025* (2013.01); *A61B 6/4452* (2013.01); *G06T 11/006* (2013.01)

(58) Field of Classification Search
 CPC ..... A61B 6/025; A61B 6/5205; G06T 11/005; G06T 11/006
 See application file for complete search history.

(56) References Cited

U.S. PATENT DOCUMENTS

| 6,002,739 A | 12/1999 | Heumann |
| 9,861,332 B2* | 1/2018 | Fukuda ............... A61B 6/5205 |
| 2004/0264636 A1 | 12/2004 | Claus et al. |
| 2012/0321163 A1 | 12/2012 | Akahori |
| 2016/0081644 A1* | 3/2016 | Fukuda ............... A61B 6/5205 378/4 |
| 2016/0081645 A1* | 3/2016 | Fukuda ............... A61B 6/5205 378/4 |
| 2017/0071554 A1* | 3/2017 | Fukuda ............... A61B 6/4452 |
| 2017/0086770 A1* | 3/2017 | Morita ................. A61B 6/032 |
| 2017/0231593 A1* | 8/2017 | Fukuda ................ A61B 6/032 382/132 |

FOREIGN PATENT DOCUMENTS

| JP | 11-339050 A | 12/1999 |
| JP | 2005-013736 A | 1/2005 |
| JP | 2013-000261 A | 1/2005 |
| JP | 2013-031641 A | 2/2013 |

* cited by examiner

*Primary Examiner* — Thomas R Artman
(74) *Attorney, Agent, or Firm* — Birch, Stewart, Kolasch & Birch, LLP

(57) ABSTRACT

An image obtaining unit obtaining a plurality of projection images taken by imaging a subject with different radiation source positions. A pixel value projecting unit projects pixel values of the projection images on coordinate positions on a desired slice plane of the subject based on the positional relationship between the radiation source position with which each projection image is taken and the radiation detector, while preserving pixel values of the projection images. A pixel value calculating unit calculates a pixel value at each coordinate position of interest on the slice plane based on a plurality of pixel values of the projection images projected in a predetermined range relative to the coordinate position of interest on the slice plane to thereby generate a tomographic image of the slice plane.

20 Claims, 9 Drawing Sheets

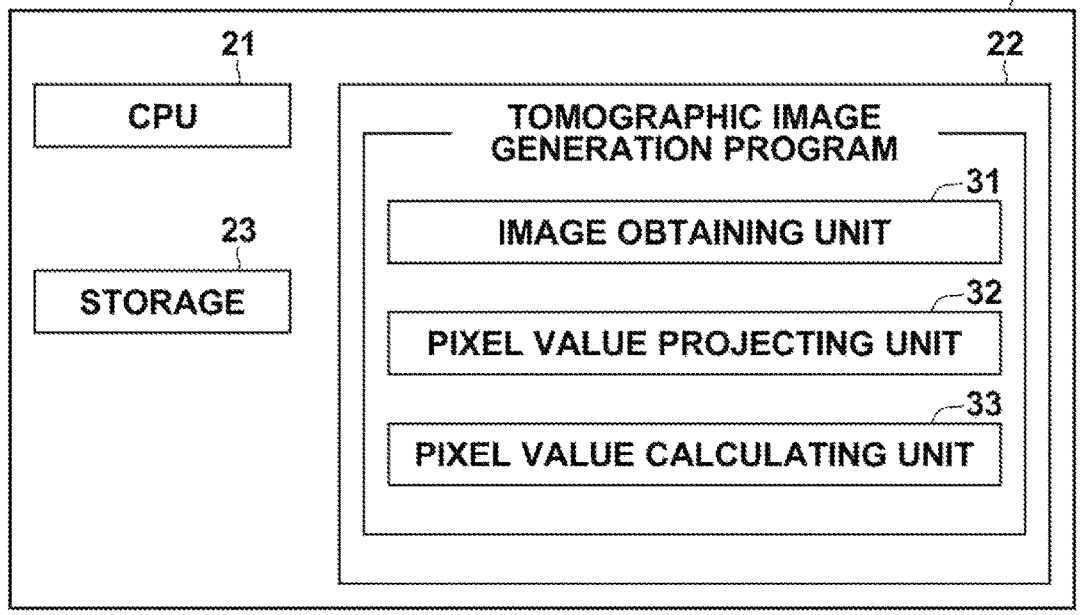
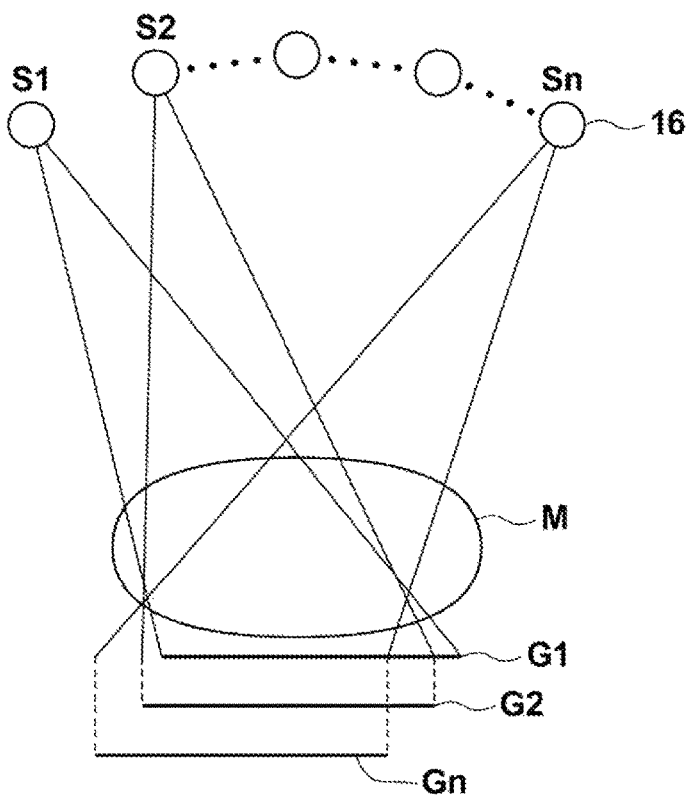

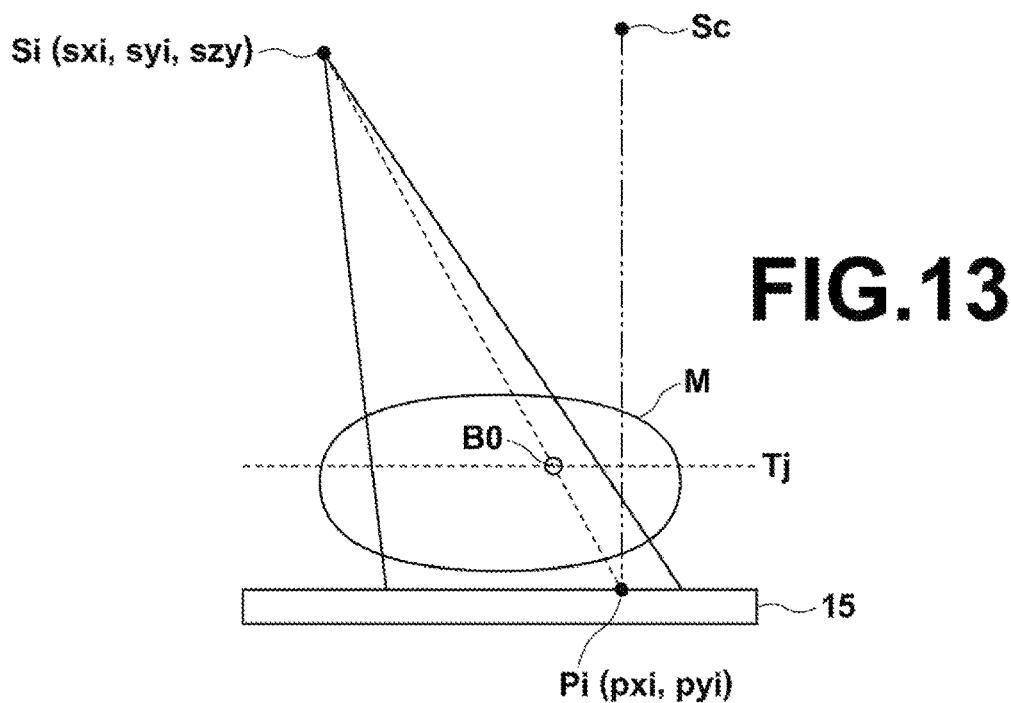
FIG.13
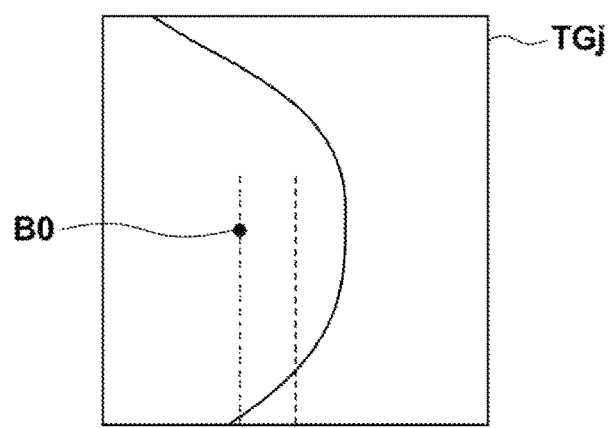
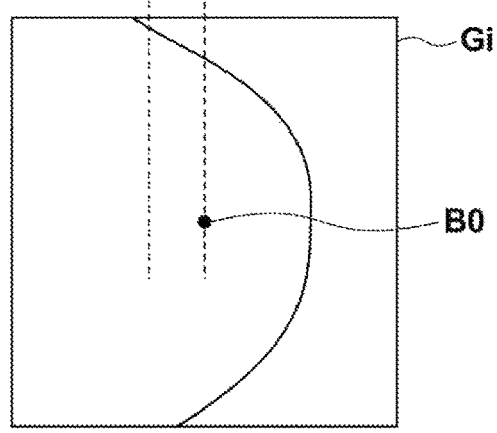
FIG.14

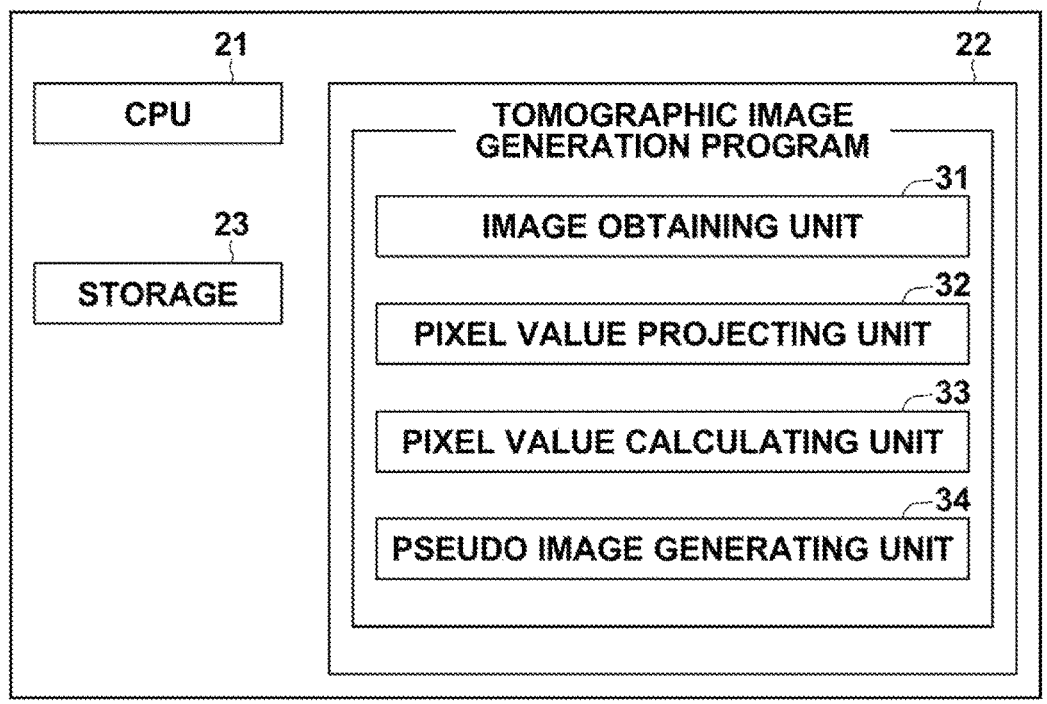
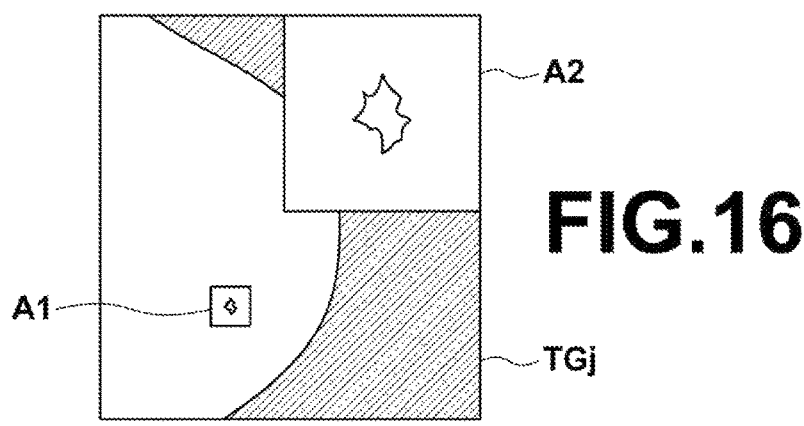

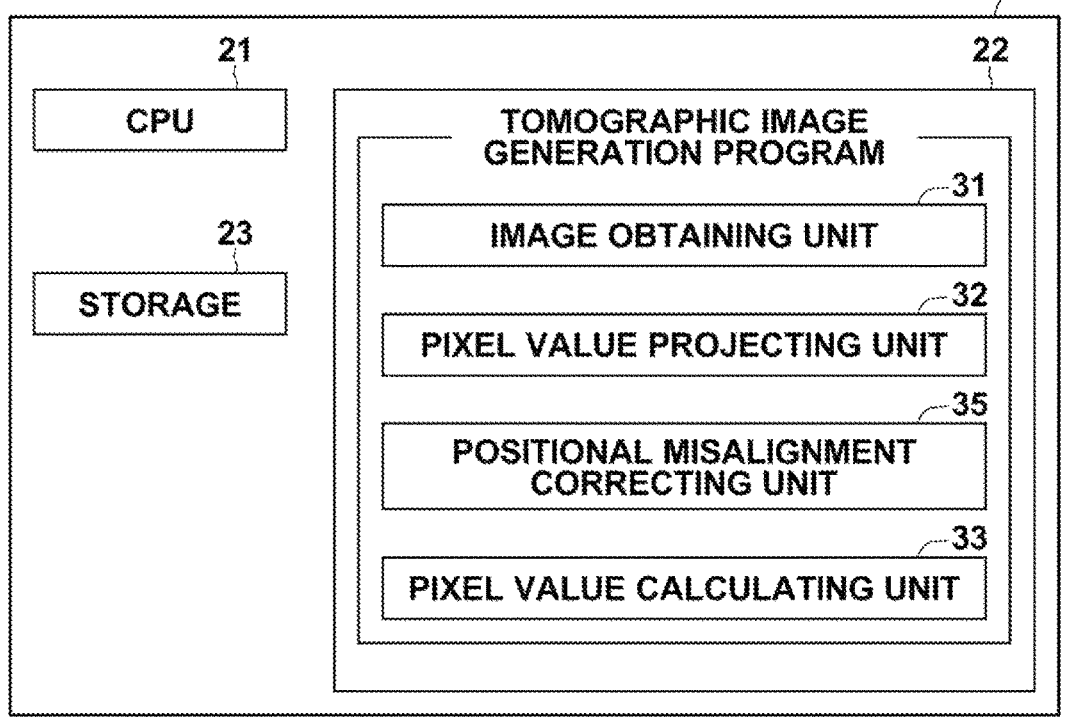
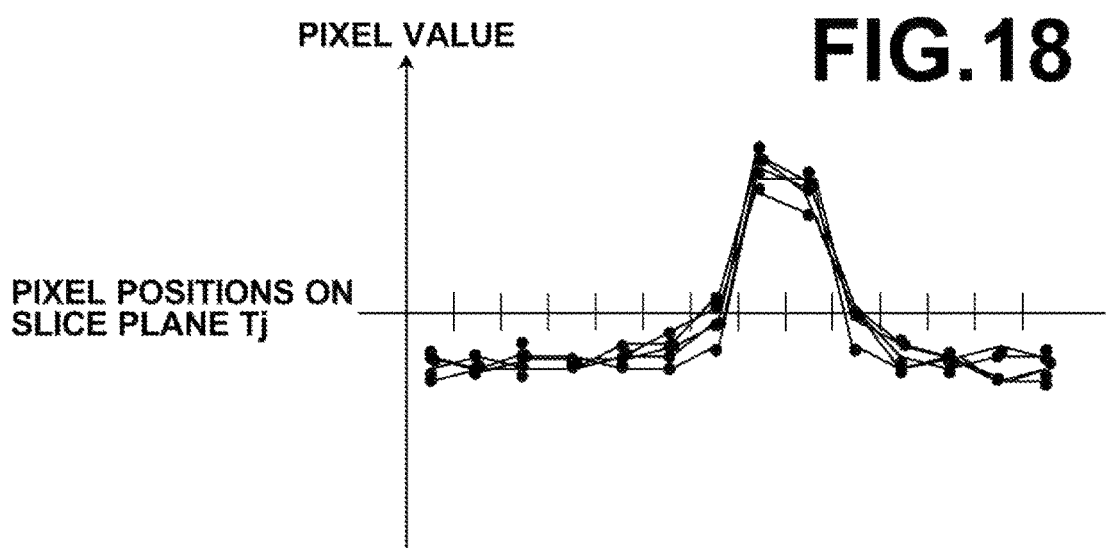

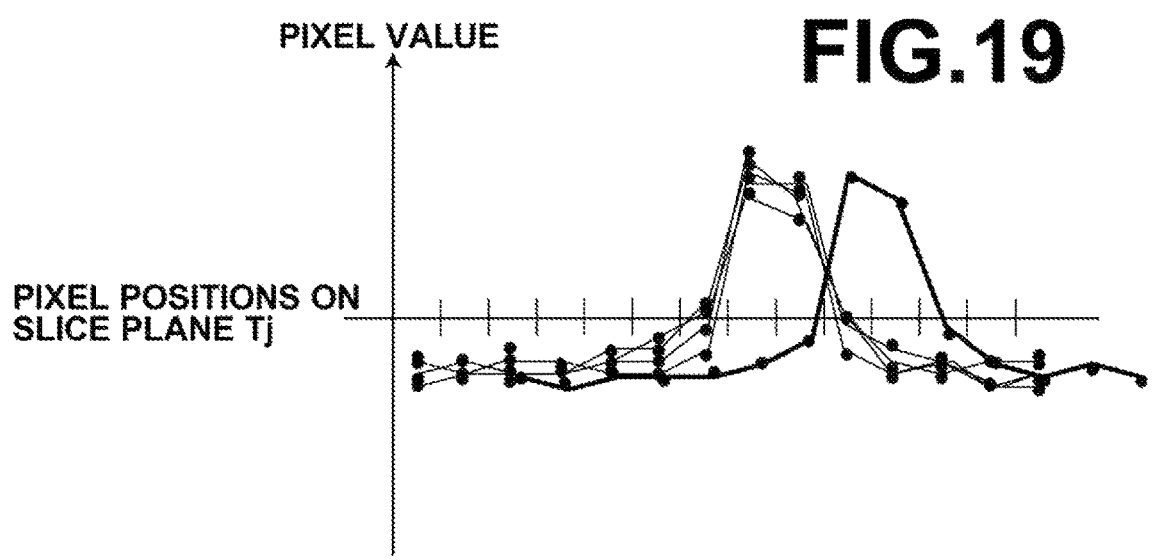

TOMOGRAPHIC IMAGE GENERATION DEVICE AND METHOD, AND RECORDING MEDIUM

CROSS-REFERENCE TO RELATED APPLICATIONS

The present application claims priority under 35 U.S.C. § 119 to Japanese Patent Application No. 2014-190784, filed on Sep. 19, 2014 and Japanese Unexamined Patent Application No. 2015-162559 filed on Aug. 20, 2015. Each of the above application(s) is hereby expressly incorporated by reference, in its entirety, into the present application.

BACKGROUND

The present disclosure relates to a tomographic image generation device, a tomographic image generation method and a tomographic image generation program for obtaining a plurality of projection images of a subject by imaging the subject with different radiation source positions, and generating a tomographic image from the projection images.

In recent years, in order to more closely observe an affected part of the body with a radiographic imaging apparatus using radiation, such as x-ray or γ-ray, tomosynthesis imaging has been proposed, in which imaging is performed by applying radiation to the subject from different radiation source positions by moving the radiation source, and the thus obtained projection images are added up to generate a tomographic image in which a desired slice plane is emphasized. In the tomosynthesis imaging, a plurality of projection images are obtained by imaging a subject with different radiation source positions by moving the radiation source in parallel with the radiation detector or along a circular or ellipsoidal arc trajectory depending on characteristics of the imaging apparatus and necessary tomographic images, and the projection images are reconstructed to generate a tomographic image using a simple reverse projection method, or a reverse projection method such as a filter reverse projection method.

However, with the tomosynthesis imaging, angles at which the radiation can be applied to the subject are limited, and there may be cases where a tomographic image reconstructed from the projection images by a reverse projection method, for example, includes an artifact which is a virtual image of a structure in an area of the tomographic image where the structure in the subject is not actually present. More specifically, the reverse projection may introduce an artifact of a structure in an area where the structure is not actually present of the tomographic image of a slice plane, which is different from a tomographic image of a slice plane where the structure is present. When such an artifact is too visible, it is difficult to see a structure, such as a lesion, which is necessary for diagnosis.

During the tomosynthesis imaging, the radiation is applied to the subject at a plurality of times, and a radiation dose as low as possible is used for each time to reduce the radiation exposure of the subject. However, a low radiation dose results in more quantum noise of radiation in the projection images obtained by the imaging, which in turn results in more visible noise in the reconstructed tomographic image.

Various techniques for reducing such an artifact or noise have been proposed. For example, Japanese Unexamined Patent Publication No. 2013-000261 (hereinafter, Patent Document 1) has proposed a technique which involves: calculating a similarity between each pixel of a reference projection image which is one of projection images and the corresponding pixel of each of the other projection images, which pixels are cumulatively added on the same position on a tomographic image; calculating a weighting factor for each pixel of the projection images such that the weighting factor is greater when the similarity is higher; and reconstructing the tomographic image by calculating a cumulative addition of products calculated by multiplying each pixel value of each projection image with the corresponding weighting factor.

Besides the above-described technique, techniques called an algebraic reconstruction method or a iterative approximation reconstruction method have also been proposed. These techniques calculate a tomographic image such that images formed by projecting the reconstructed tomographic image agree with the actually taken projection images. These techniques allow incorporating various mathematical models in the reconstruction, thereby allowing taking the artifact correction, the noise reduction, etc., into account to generate a tomographic image with suppressed artifacts and reduced noise.

However, the technique taught in Patent Document 1 and the reconstruction process such as the iterative approximation reconstruction method have a drawback that they require very long calculation time. To address this problem, a technique for reducing artifacts while reducing the calculation time has been proposed, which involves: generating a plurality of bandlimited images with different frequency response characteristics from projection images; performing nonlinear transformation on the bandlimited images such that portions that exceed a predetermined value of the bandlimited images become small; adding up the bandlimited images after the nonlinear transformation to generate a plurality of transformed images; and reconstructing a tomographic image from the transformed images (see Japanese Unexamined Patent Publication No. 2013-031641, hereinafter, Patent Document 2).

Japanese Unexamined Patent Publication Nos. 2005-013736 and 11(1999)-339050 (hereinafter, Patent Documents 3 and 4, respectively) have proposed techniques to improve the calculation speed for reconstructing a tomographic image by setting the pixel size of the tomographic image the same as the pixel size of the radiation detector regardless of the height of the slice plane.

SUMMARY

While the technique taught in Patent Document 2 allows reducing artifacts, it does not consider reducing noise. When it is attempted to reduce the calculation time, as taught in Patent Documents 2 to 4, sufficient reduction of artifacts may not be achieved. Further, in the techniques taught in Patent Document 1 to 4, the pixel value at each pixel position of interest on the tomographic image is calculated by adding up only the pixel values at pixel positions on the projection images corresponding to the pixel position of interest. Therefore influence of noise or artifacts cannot be reduced sufficiently by performing the weighting or the nonlinear transformation.

In view of the above-described circumstances, the present disclosure is directed to improve the image quality of a tomographic image generated from a plurality of projection images obtained by imaging, such as tomosynthesis imaging, with different radiation source positions, while reducing the calculation time.

An aspect of a tomographic image generation device according to the disclosure comprises:

an image obtaining unit for obtaining a plurality of projection images corresponding to different radiation source positions, the projection images being taken by moving a radiation source relative to a detecting unit and applying radiation to a subject from the different radiation source positions to which the radiation source is moved;

a pixel value projecting unit for projecting pixel values of the projection images on coordinate positions on a desired slice plane of the subject based on a positional relationship between the radiation source position with which each of the projection images is taken and the detecting unit, while preserving the pixel values of the projection images; and a pixel value calculating unit for calculating a pixel value at each coordinate position of interest on the slice plane based on a plurality of pixel values of the projection images projected in a predetermined range relative to the coordinate position of interest on the slice plane to thereby generate a tomographic image of the slice plane.

The description "moving a radiation source relative to a detecting unit" as used herein encompasses cases where only the radiation source is moved, only the detecting unit is moved, and both the radiation source and the detecting unit are moved.

It should be noted that each of the projection images and the tomographic image of the slice plane is formed by a plurality of pixels which are two-dimensionally and discretely arranged at a given sampling interval, where the pixels are located at grid points corresponding to the given sampling interval. The "pixel positions" as used herein refers to positions corresponding to the grid points on which pixel values forming an image are located on the projection image or the tomographic image. On the other hand, the "coordinate positions" as used herein includes the grid points on which pixels forming a image are located, i.e., the pixel positions, and positions between the grid points, i.e., positions where pixel values forming the image are not located. That is, the coordinate positions include not only the pixel positions but also positions between the pixel positions.

The projection images to be projected may be all the projection images obtained or two or more projection images of the projection images obtained.

The "desired slice plane" as used herein refers to a slice plane of the subject for which the tomographic image is generated.

The description "while preserving the pixel values of the projection images" as used herein refers to that the pixel values of the projection images are not changed. It should be noted that, in the disclosure, the pixel value at a pixel position of the projection image may not be able to be projected on a coordinate position on the slice plane. That is, depending on the positional relationship between the radiation source position and the detecting unit, the pixel value of the projection image corresponding to the coordinate positions on the slice plane may not be at a pixel position of the projection image, but at a coordinate position between pixel positions. In such a case, the pixel value at the coordinate position on the projection image to be projected on the coordinate position on the slice plane can be calculated by interpolation using pixel values at pixel positions around the coordinate position, for example. In this case, the pixel value calculated by interpolation is also a pixel value of the projection image, and the pixel value of the projection image calculated by interpolation is projected on the corresponding coordinate position on the slice plane while being preserved.

The "coordinate position of interest on the slice plane" as used herein refers to a coordinate position for which the pixel value is calculated to generate the tomographic image of the slice plane. The tomographic image of the slice plane can be generated by calculating the pixel value at the coordinate position of interest with sequentially changing the coordinate position of interest on the slice plane.

The "predetermined range relative to the coordinate position of interest" as used herein refers to a range of a predetermined number of coordinate positions or pixel positions around and including the pixel position of interest. For example, a range of 3×3 coordinate positions or pixel positions with the pixel position of interest being the center, or a range of 5×5 coordinate positions or pixel positions with the pixel position of interest being the center may be set as the predetermined range relative to the coordinate position of interest. It should be noted that the size of the predetermined range may be fixed or may be changed arbitrarily according to input by the operator.

In the tomographic image generation device according to the disclosure, the pixel value projecting unit may project, for each of the different radiation source positions, pixel values at coordinate positions on the corresponding projection image intersecting with straight lines that connect the radiation source position and individual pixel positions on the slice plane as pixel values at the pixel positions on the slice plane on the straight lines.

In the tomographic image generation device according to the disclosure, the pixel value projecting unit may project, for each of the different radiation source positions, pixel values at pixel positions on the corresponding projection image on straight lines that connect the radiation source position and the individual pixel positions on the projection image as pixel values at coordinate positions on the slice plane intersecting with the straight lines.

In this case, a spacing between coordinate positions on the slice plane may be smaller than a spacing between pixel positions on the slice plane.

In the tomographic image generation device according to the disclosure, the pixel value calculating unit may calculate the pixel value at the coordinate position of interest by performing regression analysis on pixel values of the projection images projected on the slice plane.

The "regression analysis" is a statistical technique for analyzing a multivariate relationship. It is assumed here that observed values observed at observation points include noise added to the true values. The regression analysis is a technique to solve an inverse problem to find the true value at every observation point by regression using a least squares method, a moving average method, a kernel function, etc. In the disclosure, the pixel value at the coordinate position of interest is calculated with assuming that each coordinate position on the slice plane with the pixel values of the projection images projected thereon is the observation point, each pixel value at the observation point is the observed value, and a pixel value at the coordinate position of interest is the true value.

In the tomographic image generation device according to the disclosure, the pixel value calculating unit may calculate pixel values at pixel positions on the slice plane by performing the regression analysis to generate a regression surface that represents a tomographic image of the slice plane, and sampling the regression surface at a desired sampling interval, to thereby generate the tomographic image.

In this case, the sampling interval may be different from a sampling interval of the projection images.

By changing the sampling interval of the regression surface, the resolution of the tomographic image can be changed. For example, a smaller sampling interval results in a higher resolution of the tomographic image. The "desired sampling interval" as used herein refers to a spacing between pixels with which the tomographic image having a necessary resolution is obtained. It should be noted that the desired sampling interval may be fixed or may be changed arbitrarily according to input by the operator.

The description "different from a sampling interval of the projection images" as used herein encompasses both the cases where the sampling interval of the regression surface is greater than the sampling interval of the projection images, and where the sampling interval of the regression surface is smaller than the sampling interval of the projection images. If the sampling interval of the regression surface is greater than the sampling interval of the projection images, the resolution of the tomographic image is lower than the resolution of the projection images. In contrast, if the sampling interval of the regression surface is smaller than the sampling interval of the projection images, the resolution of the tomographic image is higher than the resolution of the projection images.

In the tomographic image generation device according to the disclosure, if an instruction to change the size of an area of interest in the tomographic image being displayed is received, the pixel value calculating unit may generate a tomographic image of the area of interest with changing the sampling interval of an area of the regression surface corresponding to the area of interest according to the instruction to change.

In the tomographic image generation device according to the disclosure, the pixel value calculating unit may change sharpness of the pixel value at the coordinate position of interest when the regression analysis is performed.

The description "change sharpness" as used herein encompasses emphasizing the sharpness such that an edge included in the generated tomographic image is emphasized, and reducing the sharpness such that the generated tomographic image is smoothed to reduce noise.

In this case, the pixel value calculating unit may change a level of change of the sharpness depending on information of at least one of imaging conditions under which the projection images are taken and a structure of the subject included in the projection images.

When the projection images are taken, a smaller amount of radiation that reaches the detector results in more noise in the projection images. The amount of noise in the projection images and the sharpness of the obtained images also vary depending on the radiation quality of the x-ray, i.e., whether the x-ray is a high voltage x-ray or a low voltage x-ray, the type of material forming the detecting unit, and/or the presence or absence of a grid used to remove scattered rays during imaging. The "imaging conditions" as used herein refer to various conditions that influence the amount of noise and the sharpness of the projection images, and examples thereof may include the amount of radiation that reaches the detector during imaging, the type of the detecting unit, and/or the presence or absence of the grid. The "structure of the subject" as used herein refers to a structure, such as an edge, included in the subject.

A preferred sharpness of the tomographic image depends on the preference of the user, such as a doctor, who observes the image. Therefore the sharpness may be changeable according to the preference of the user.

In the tomographic image generation device according to the disclosure, the pixel value calculating unit may calculate the pixel value at the coordinate position of interest with removing an outlier pixel value among the pixel values of the projection images projected in the predetermined range relative to the coordinate position of interest or weighting the outlier pixel value with a small weight.

The "outlier" as used herein refers to a pixel value that is largely different from the other pixel values among the pixel values of the projection images projected in the predetermined range relative to the coordinate position of interest. The expression "largely different" as used herein means that a difference between the value of the outlier and an average value of the pixel values projected in the predetermined range relative to the coordinate position of interest, for example, exceeds a predetermined threshold value.

In the tomographic image generation device according to the disclosure, the pixel value projecting unit may correct, based on a positional relationship between a certain radiation source position and each coordinate position of interest on the projection image corresponding to the certain radiation source position, a coordinate position on the slice plane on which a pixel value at the coordinate position of interest on the projection image is projected such that two-dimensional coordinates of the coordinate position of interest on the projection image corresponding to the certain radiation source position agrees with two-dimensional coordinates of the coordinate position on the slice plane on which the pixel value at the coordinate position of interest on the projection image is projected, and may project the pixel values of the projection images on the corrected coordinate positions on the slice plane.

In this case, the image obtaining unit may obtain a radiographic image of the subject taken by applying the radiation to the subject from the certain radiation source position, the pixel value calculating unit may generate the tomographic image by calculating the pixel value at the coordinate position of interest on the slice plane with the pixel values of the projection images being projected on the corrected coordinate positions, and the tomographic image generation device may further comprise a display unit for displaying the radiographic image and the tomographic image.

The "radiographic image of the subject" as used herein refers to an image including a transmission image of a structure included in the subject, which image being obtained by imaging the subject under imaging conditions for obtaining a transmission image of the subject with the radiation source position being fixed at the certain radiation source position.

In the tomographic image generation device according to the disclosure, the pixel value projecting unit and the pixel value calculating unit may generate the tomographic image for each of a plurality of slice planes of the subject, and the tomographic image generation device may further comprise a pseudo image generating unit for generating a pseudo image from the tomographic images.

The "pseudo image" as used herein refers to a pseudo image that appears as an image of a type different from the tomographic image. An example thereof is an addition tomographic image that is generated by simply adding up pixel values at corresponding pixel positions of the tomographic images so that it appears as a transmission image obtained by ordinary radiographic imaging. Besides the addition tomographic image, a maximum projection image that appears as a three-dimensional image obtained by an MIP (Maximum Intensity Projection) method that extracts maximum values from corresponding pixel positions of the tomographic images, and a minimum projection image that appears as a three-dimensional image obtained by a minIP (Minimum Intensity Projection) method that extracts minimum values from corresponding pixel positions of the tomographic images can be used as the pseudo image.

In the tomographic image generation device according to the disclosure, the pixel value calculating unit may calculate weighting factors based on a difference between the pixel value at the coordinate position of interest and the pixel value at the coordinate position of each projection image corresponding to the coordinate position of interest, and may calculate the pixel value at the coordinate position of interest again based on the plurality of pixel values of the projection images and the weighting factors to calculate a new pixel value at the coordinate position of interest.

In this case, the pixel value calculating unit may iterate calculating new weighting factors using the new pixel value at the coordinate position of interest, and calculating a new pixel value at the coordinate position of interest again based on the plurality of pixel values of the projection images and the new weighting factors.

As the "weighting factor", for example, a smaller value may be used for a larger difference between the pixel value at the coordinate position of interest and each pixel value at the coordinate position of each projection image corresponding to the coordinate position of interest.

The number of iterations of the process of calculating new weighting factors using the new pixel value at the coordinate position of interest, and calculating a new pixel value at the coordinate position of interest again based on the plurality of pixel values of the projection images and the new weighting factors may be set in advance, or the process may be iterated until a given convergence condition, such that a difference between the new pixel value at the coordinate position of interest and each pixel value at the coordinate position of each projection image corresponding to the coordinate position of interest is not greater than a predetermined threshold value, is satisfied.

An aspect of a tomographic image generation method according to the disclosure comprises the steps of:

obtaining a plurality of projection images corresponding to different radiation source positions, the projection images being taken by moving a radiation source relative to a detecting unit and applying radiation to a subject from the different radiation source positions to which the radiation source is moved;

projecting pixel values of the projection images on coordinate positions on a desired slice plane of the subject based on a positional relationship between the radiation source position with which each of the projection images is taken and the detecting unit, while preserving the pixel values of the projection images; and calculating a pixel value at each coordinate position of interest on the slice plane based on a plurality of pixel values of the projection images projected in a predetermined range relative to the coordinate position of interest on the slice plane to thereby generate a tomographic image of the slice plane.

The tomographic image generation method according to the disclosure may be provided in the form of a program for causing a computer to execute the tomographic image generation method.

According to the present disclosure, pixel values of the projection images are projected on coordinate positions on a desired slice plane of the subject based on the positional relationship between the radiation source position with which each of the projection images is taken and the detecting unit, while preserving the pixel values of the projection images. Then, the pixel value at each coordinate position of interest is calculated based on a plurality of pixel values of the projection images projected in a predetermined range relative to the coordinate position of interest on the slice plane to generate a tomographic image. When compared with the conventional techniques where only the pixel values of the projection images projected on the coordinate position of interest are used to calculate the pixel value at the coordinate position of interest, the disclosure allows taking influence of pixel values around the coordinate position of interest into account, thereby reducing artifacts to allow generation of a tomographic image with even higher image quality. Further, since it is not necessary to repeat projecting the pixel values again and again, which is necessary in the iterative approximation reconstruction method, significant reduction of the calculation time can be achieved.

BRIEF DESCRIPTION OF THE DRAWINGS

FIG. 3 is a diagram illustrating the schematic configuration of the tomographic image generation device of the first embodiment implemented by installing a tomographic image generation program on a computer, FIG. 4 is a diagram for explaining how projection images are obtained, FIG. 13 is a diagram showing a positional relationship between the position of a structure on a slice plane and the position of the structure projected on a radiation detector, FIG. 14 is a diagram showing a difference between the position of a structure on a tomographic image and the position of the structure on a radiographic image, FIG. 15 is a diagram illustrating the schematic configuration of a tomographic image generation device of a fourth embodiment implemented by installing a tomographic image generation program on a computer, FIG. 16 shows a state where an enlarged image of an area of interest is displayed on a display unit, FIG. 17 is a diagram illustrating the schematic configuration of a tomographic image generation device of a fifth embodiment implemented by installing a tomographic image generation program on a computer, FIG. 18 shows a plurality of slice plane projection images without positional misalignment, FIG. 19 shows a plurality of slice plane projection images with positional misalignment.

DETAILED DESCRIPTION OF THE PREFERRED EMBODIMENTS

Figure 1:
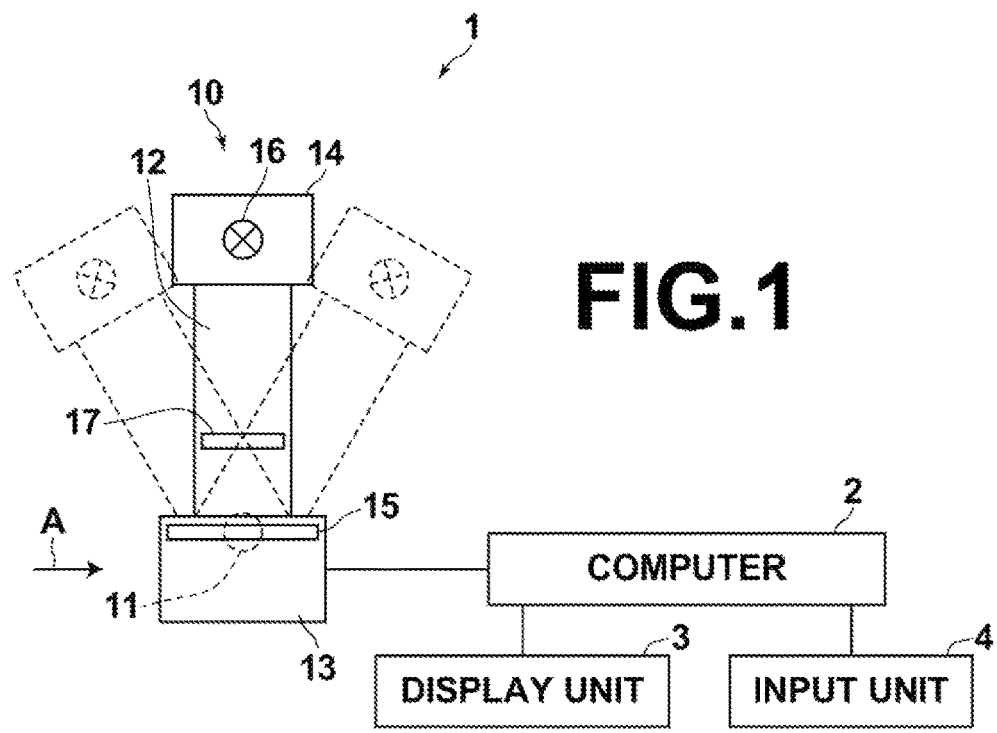
FIG. 1 is a diagram illustrating the schematic configuration of a radiographic imaging apparatus to which a tomographic image generation device according to a first embodiment of the disclosure is applied.
Figure 2:
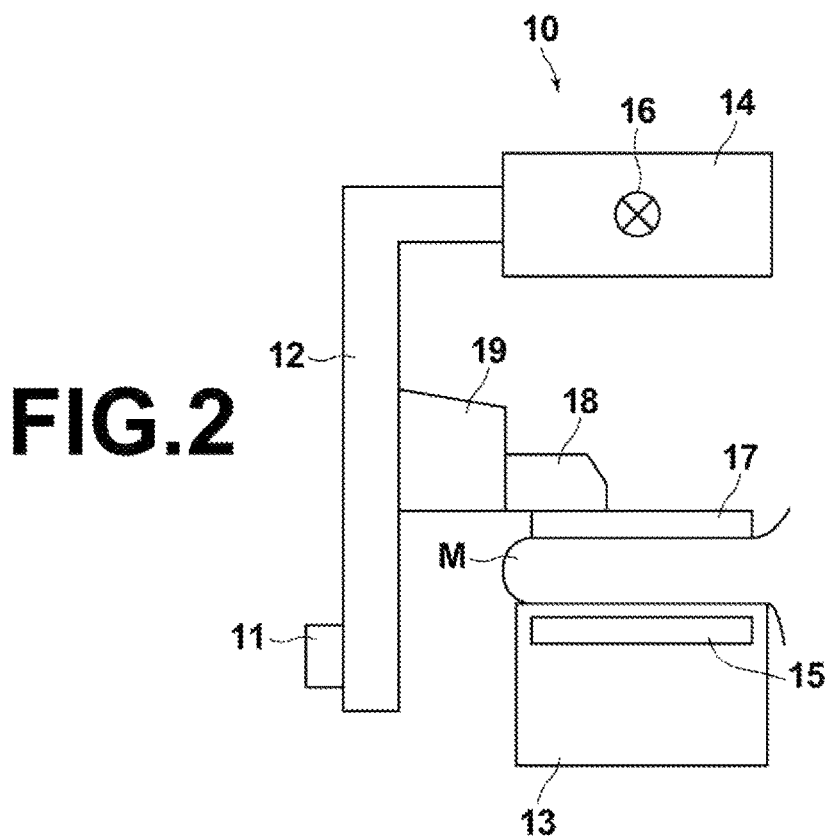
FIG. 2 is a diagram illustrating the radiographic imaging apparatus viewed from the direction of arrow A in FIG. 1.

Hereinafter, embodiments of the present disclosure will be described with reference to the drawings. FIG. 1 is a diagram illustrating the schematic configuration of a radiographic imaging apparatus to which a tomographic image generation device according to a first embodiment of the disclosure is applied, and FIG. 2 is a diagram illustrating the radiographic imaging apparatus viewed from the direction of arrow A in FIG. 1. The radiographic imaging apparatus 1 is a mammographic apparatus that images a breast M (which may hereinafter also be referred to as "subject M") with different radiation source positions, which correspond to different imaging directions, and obtains a plurality of radiographic images, i.e., projection images, to generate a tomographic image of the breast by performing tomosynthesis imaging. As shown in FIG. 1, the radiographic imaging apparatus 1 includes an imaging unit 10, a computer 2 connected to the imaging unit 10, and a display unit 3 and an input unit 4 connected to the computer 2.

The imaging unit 10 includes an arm 12, which is coupled to a base (not shown) via a rotatable shaft 11. An imaging table 13 is attached to one end of the arm 12, and a radiation applying unit 14 is attached to the other end of the arm 12 so as to face the imaging table 13. The arm 12 is configured such that only the end to which the radiation applying unit 14 is attached can be rotated, this allows only the radiation applying unit 14 to be rotated while the imaging table 13 is fixed. Rotation of the arm 12 is controlled by the computer 2.

The imaging table 13 includes therein a radiation detector 15 (detecting unit), such as a flat panel detector. The imaging table 13 also includes therein a circuit board, etc., which includes a charge amplifier for converting an electric charge signal read out from the radiation detector 15 into a voltage signal, a correlated double sampling circuit for sampling the voltage signal outputted from the charge amplifier, an AD converter for converting the voltage signal into a digital signal, etc.

The radiation detector 15 is of a type that is repeatedly usable to record and read out a radiographic image on and from it. The radiation detector 15 may be a so-called direct-type radiation detector, which directly receives the radiation and generates electric charges, or may be a so-called indirect-type radiation detector, which once converts the radiation into visible light, and then converts the visible light into electric charge signals. As the reading system to read out the radiographic image signal, it is desirable to use a so-called TFT reading system, which reads out the radiographic image signal with turning on and off TFT (thin film transistor) switches, or a so-called optical reading system, which reads out the radiographic image signal by applying reading light. However, this is not intended to limit the invention and any other type of radiation detector may be used.

The radiation applying unit 14 contains therein a x-ray source 16 (radiation source). Timing of application of radiation from the x-ray source 16 and x-ray generation conditions (such as tube current, time, tube current time product, etc.) of the x-ray source 16 are controlled by the computer 2.

To the arm 12, a compression paddle 17 disposed above the imaging table 13 for compressing the breast M, a support 18 for supporting the compression paddle 17, and a moving mechanism 19 for moving the support 18 in the vertical direction as in FIGS. 1 and 2 are attached.

The display unit 3 is a display device, such as a CRT or a liquid crystal monitor. The display unit 3 displays projection images which are obtained as described later, a generated tomographic image, and messages necessary for operation, etc. The display unit 3 may include a built-in speaker for outputting sound.

The input unit 4 is formed by a keyboard, a mouse, and/or a touch-panel input device. The input unit 4 receives operation by the operator of the radiographic imaging apparatus 1. The input unit 4 also receives input of various information, such as imaging conditions, necessary for performing tomosynthesis imaging, and instructions to modify the information. In this embodiment, the individual units of the radiographic imaging apparatus 1 operate according to the information inputted by the operator via the input unit 4.

A tomographic image generation program is installed on the computer 2. In this embodiment, the computer may be a work station or a personal computer which is directly operated by the operator, or may be a server computer connected to the work station or the personal computer via a network. The tomographic image generation program is distributed with being recorded on a recording medium, such as a DVD or a CD-ROM, and is installed on the computer from the recording medium. Alternatively, the tomographic image generation program is stored in a storage device of a server computer connected to a network or a network storage such that it is externally accessible, and is downloaded and installed on the computer as necessary.

FIG. 3 is a diagram illustrating the schematic configuration of the tomographic image generation device implemented by installing the tomographic image generation program on the computer 2. As shown in FIG. 3, the tomographic image generation device includes a CPU 21, a memory 22, and a storage 23, as the configuration of a standard computer.

The storage 23 is formed by a storage device, such as a hard disk or SSD. The storage 23 stores various information including programs for driving the individual units of the radiographic imaging apparatus 1, and the tomographic image generation program. The storage 23 also stores projection images obtained by tomosynthesis imaging, and a tomographic image which is generated as described later.

The memory 22 temporarily stores the programs stored in the storage 23 for the CPU 21 to execute various operations. The tomographic image generation program defines, as the operations to be executed by the CPU 21: an image obtaining operation for causing the radiographic imaging apparatus 1 to perform tomosynthesis imaging to obtain a plurality of projection images of the breast M; a pixel value projecting operation for projecting pixel values of the projection images on coordinate positions on a desired slice plane of the breast M, which is the subject, based on the positional relationship between the position of the x-ray source 16 with which each projection image is taken and the radiation detector 15, while preserving the pixel values of the projection images; and a pixel value calculating operation for calculating a pixel value of each coordinate position of interest based on the pixel values of the projection images projected in a predetermined range relative to the coordinate position of interest on the desired slice plane to generate a tomographic image.

When the CPU 21 executes the above-described operations according to the tomographic image generation program, the computer 2 functions as an image obtaining unit 31, a pixel value projecting unit 32, and a pixel value calculating unit 33. It should be noted that the computer 2 may include CPUs for executing the image obtaining operation, the pixel value projecting operation, and the pixel value calculating operation, respectively.

The image obtaining unit 31 causes the arm 12 to rotate about the rotatable shaft 11 to move the x-ray source 16, applies an x-ray to the breast M, which is the subject, from different radiation source positions to which the x-ray source 16 is moved, and detects the x-ray transmitted through the breast M with the radiation detector 15 to obtain a plurality of projection images Gi (i=1 to n, where n is the number of radiation source positions) corresponding to the different radiation source positions. FIG. 4 is a diagram for explaining how the projection images Gi are obtained. As shown in FIG. 4, the x-ray source 16 is moved to each of radiation source positions S1, S2, . . . , Sn, and the x-ray source 16 is activated at each radiation source position to apply an x-ray to the breast M. Then, the x-ray transmitted through the breast M is detected with the radiation detector 15 to obtain projection images G1, G2, . . . , Gn corresponding to the radiation source positions S1 to Sn. The obtained projection images Gi are stored in the storage 23. It should be noted that the projection images Gi may be obtained and stored in the storage 23 according to a program separate from the tomographic image generation program. In this case, the image obtaining unit 31 reads out the projection images Gi, which are stored in the storage 23, from the storage 23 for the pixel value projecting operation and the pixel value calculating operation.

In this embodiment, all the projection images Gi stored in the storage 23 may be read out to be used for the pixel value projecting operation and the pixel value calculating operation, or a predetermined number of (two or more) projection images Gi among the projection images Gi stored in the storage 23 may be read out to be used for the pixel value projecting operation and the pixel value calculating operation.

Figure 5:
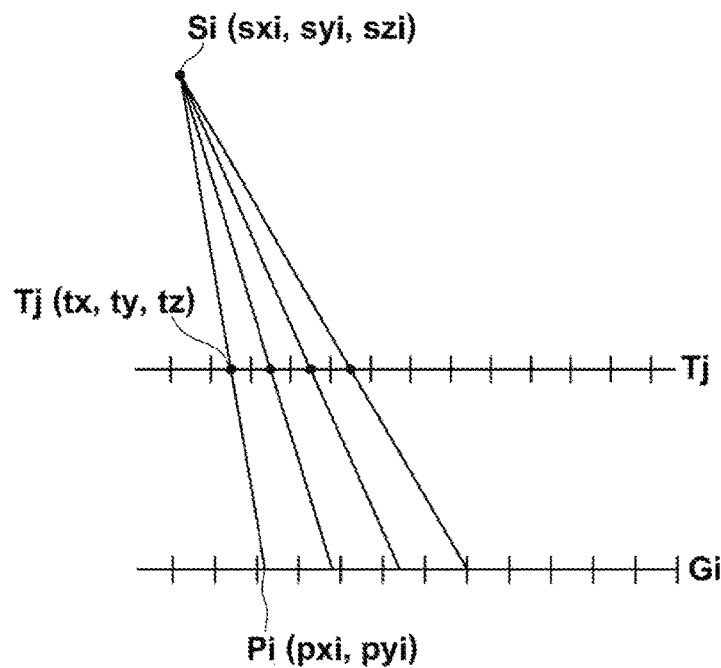
FIG. 5 is a diagram for explaining how pixel values are projected in the first embodiment.

The pixel value projecting unit 32 projects pixel values of the projection images obtained by the image obtaining unit 31 on coordinate positions on a desired slice plane of the breast M while preserving the pixel values of the projection images. FIG. 5 is a diagram for explaining how the pixel values are projected in the first embodiment. It should be noted that FIG. 5 explains a case where a projection image Gi obtained with a radiation source position Si is projected on a desired slice plane Tj (j=1 to m, where m is the number of slice planes) of the breast M.

Figure 11:
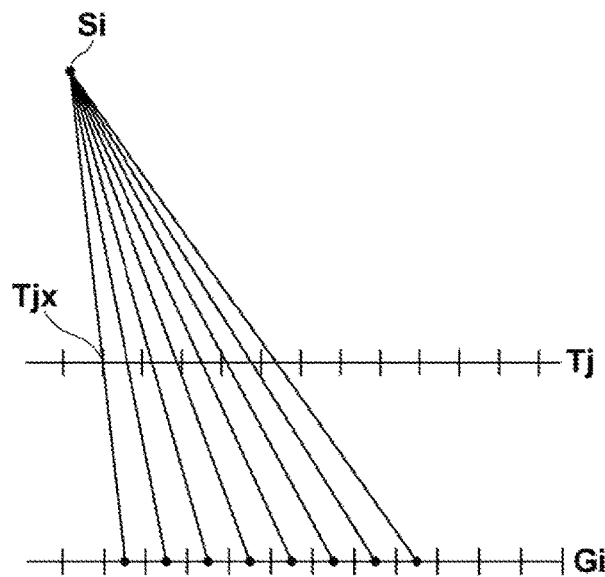
FIG. 11 is a diagram for explaining how pixel values are projected in a second embodiment.

Each of the projection image Gi and the tomographic image of the slice plane Tj, which is generated as described later, is formed by a plurality of pixels which are two-dimensionally and discretely arranged at a given sampling interval, where the pixels are located at grid points corresponding to the given sampling interval. In FIG. 5 and FIG. 11, which will be described later, the short line segments orthogonally crossing the projection image Gi and the slice plane Tj represent boundary positions between the pixels. In FIG. 5 and FIG. 11, which will be described later, each center position between the pixel boundary positions is a pixel position, which is the grid point. As shown in FIG. 5, in the first embodiment, pixel values at positions on the projection image Gi intersecting with the straight lines that connect the radiation source position Si and the individual pixel positions on the slice plane Tj are projected as pixel values at the pixel positions on the slice plane Tj on the corresponding straight lines.

Assuming that coordinates of the radiation source position Si are (sxi, syi, szi), and coordinates of a pixel position on the slice plane Tj are Tj(tx, ty, tz), coordinates (pxi, pyi) of the corresponding coordinate position Pi on the projection image Gi are expressed by the equations (1) below. In this embodiment, the z-axis is set in the direction perpendicular to the detection surface of the radiation detector 15, the y-axis is set in the direction parallel to the direction in which the position of the x-ray source 16 on the detection surface of the radiation detector 15 is moved, and the x-axis is set in the direction orthogonal to the y-axis.

$$pxi=(tx \times szi - sxi \times tz)/(szi-tz),$$

$$pyi=(ty \times szi - syi \times tz)/(szi-tz) \qquad (1).$$

Figure 6:
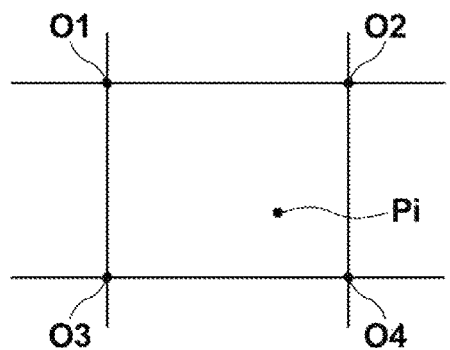
FIG. 6 is a diagram for explaining how a pixel value of a projection image is interpolated.

It should be noted that the coordinate position Pi on the projection image Gi may not be a pixel position on the projection image Gi. For example, as shown in FIG. 6, a coordinate position Pi on the projection image Gi may be between four pixel positions O1 to O4 on the projection image Gi. In this case, interpolation calculation is performed using pixel values at the four pixel positions O1 to O4, which are nearest to the coordinate position Pi of the projection image Gi, as shown in FIG. 6, to calculate the pixel value at the coordinate position Pi, and the calculated pixel value is projected on the pixel position Tj(tx, ty, tz) on the slice plane Tj. As the interpolation calculation, any technique, such as linear interpolation calculation where the pixel values at the four pixel positions are weighted depending on the distance between the coordinate position Pi and each of the four pixel positions, non-linear bicubic interpolation calculation using pixel values at more pixel positions around the coordinate position Pi, or B-spline interpolation calculation, may be used. In place of performing the interpolation calculation, the pixel value at the pixel position which is nearest to the coordinate position Pi may be used as the pixel value at the coordinate position Pi.

Figure 7:
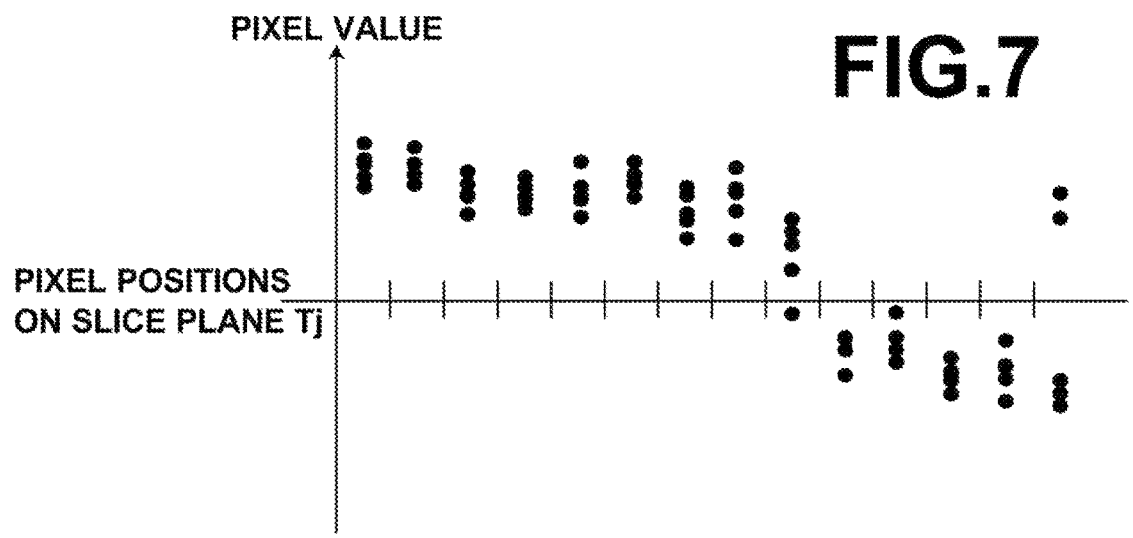
FIG. 7 shows pixel values projected on a slice plane in the first embodiment.

The pixel value projecting unit 32 projects, for each radiation source position Si, the pixel values of the corresponding projection image Gi on the slice plane Tj. As a result, n pixel values corresponding to the number of projection images are projected on each pixel position on the slice plane Tj, as shown in FIG. 7. FIG. 7 shows a state where pixel values of five projection images are projected on each pixel position. In FIG. 7, and in FIGS. 8, 9, 12, 18, and 19, which will be described later, the short line segments orthogonally crossing the slice plane Tj represent boundary positions between pixels, and the center positions between the pixel boundary positions are the pixel positions, which are the grid points.

The pixel value calculating unit 33 generates a tomographic image of the slice plane Tj by calculating each pixel value on the slice plane Tj. Specifically, the pixel value at each coordinate position of interest is calculated based on a plurality of pixel values of the projection images projected in a predetermined range relative to the coordinate position of interest for which the pixel value is calculated. The coordinate position of interest may be a pixel position on the slice plane Tj. While the pixel values of the projection images Gi are projected on the pixel positions on the slice plane Tj in the first embodiment, the pixel value at each coordinate position of interest may be calculated using the pixel values projected on the coordinate position of interest, or without using the pixel values projected on the coordinate position of interest. Now, how the pixel value at each coordinate position of interest is calculated is described.

The pixel values of the projection images Gi projected on the slice plane Tj by the pixel value projecting unit 32 tend to be more similar when they are nearer to each other. Therefore the pixel value calculating unit 33 performs an operation to change the sharpness such that the pixel values projected on the slice plane Tj are smoothly continuous. In this embodiment, the pixel values projected on the slice plane Tj are filtered with a smoothing filter. Specifically, pixel values at pixel positions in a predetermined range, such as 3×3 or 5×5, with the coordinate position of interest being the center are filtered with a Gaussian filter, for example. With this, the pixel values of pixels at and around the coordinate position of interest become smoothly continuous, thereby suppressing noise, such as quantum noise, which is originally included in the projection images Gi, in the pixel values projected on the slice plane Tj.

A value defining the size of the predetermined range may be stored as a fixed value in the storage 23. Further, the value may be changed arbitrarily according to input by the operator via the input unit 4. In this case, the value defining the size of the predetermined range stored in the storage 23 is rewritten according to input by the operator via the input unit 4 and the size of the predetermined range is changed.

The level of smoothness, i.e., the level of noise suppression can be changed by changing the filter size of the Gaussian filter. Specifically, increasing the filter size to increase the range of filtering with the coordinate position of interest being the center allows higher level of noise suppression. It should be noted that a lower amount of x-ray reaching the radiation detector 15 when the projection images Gi are taken results in more noise in the projection images Gi, which in turn results in more noise in the pixel values projected on the slice plane Tj. The amount of noise in the projection images Gi also varies depending on the radiation quality of the x-ray, i.e., whether the x-ray is a high voltage x-ray or a low voltage x-ray. The amount of noise in the projection images Gi also varies depending on the type of the radiation detector 15 used to take the projection images. Further, in some cases, a scattered ray removing grid may be disposed between the radiation detector 15 and the subject M when the projection images Gi are taken in order to prevent influence of scattered ray of the x-ray on the subject M. The amount of noise in the projection images Gi also varies depending on the type of the scattered ray removing grid, or the presence or absence of the scattered ray removing grid.

For this reason, in this embodiment, properties of the smoothing filter are changed based on the imaging conditions, such as the amount of x-ray reaching the radiation detector 15, the radiation quality of the x-ray, the type of the radiation detector 15, the type of the scattered ray removing grid, and the presence or absence of the scattered ray removing grid. For example, for the imaging conditions which result in more noise in the projection images Gi, the filter size is increased so that higher level of noise suppression is achieved.

When a Gaussian filter is used for the filtering, edges which are structures of the subject M included in the tomographic image, which is generated as described later, may be blurred. For this reason, the filtering may be performed using a bilateral filter which weights neighboring pixels around the coordinate position of interest depending on the distance between the pixels, and also weights the neighboring pixels around the coordinate position of interest with normally distributed weights such that the weight is smaller when the difference between pixel values is greater. Alternatively, the filtering may be achieved using a non-local means filter which performs weighting based on similarity between a neighboring area around the coordinate position of interest on the slice plane Tj and a neighboring area around an arbitrary pixel on the slice plane Tj. This allows suppressing noise while preserving edges, thereby preventing lowering of the sharpness of the tomographic image which is generated as described later.

Further, the pixel values projected on the slice plane Tj may be filtered with a differential filter, for example, to detect an edge which is the structure of the subject, where there is a sudden change in the pixel value exceeding a predetermined threshold value, and the filter properties may be changed such that the filtering is applied along the direction in which the edge extends, to thereby change the level of change of the sharpness. Still further, the filtering may be performed such that, with respect to pixel values along a boundary of an edge, pixel values at positions beyond the edge are not used. This allows preventing the edge from being smoothed, thereby preventing lowering of the sharpness of the distribution of the pixel values projected on the slice plane Tj while suppressing noise.

In place of or in addition to the smoothing, an operation to emphasize the sharpness may be performed to emphasize edges. In this case, it is preferred to perform the operation to emphasize the sharpness along the direction in which each edge extends.

After the filtering is performed as described above, the pixel value calculating unit 33 performs regression analysis on the pixel values of the projection images projected on the slice plane Tj to generate a curved surface, or a regression surface, that represents a tomographic image of the slice plane Tj. In the following description, the regression surface is considered as a regression curve for ease of explanation. The regression analysis is a statistical technique for analyzing a multivariate relationship. It is assumed here that observed values observed at observation points include noise added to the true values. The regression analysis is a technique to solve an inverse problem to find the true value at every observation point by regression using a least squares method, a moving average method, a kernel function, etc. In the first embodiment, a pixel value $r_m$ at each coordinate position of interest $u_m$ is calculated by the regression analysis with assuming that each coordinate position on the slice plane Tj with the pixel values of the projection images Gi projected thereon is an observation point $u_k$, each pixel value of the projection images projected on the observation point $u_k$ is an observed value $q_k$, and the pixel value calculated for the coordinate position of interest $u_m$ is a true value $r_m$.

In the case where a least squares method is used, it is assumed that the true value follows a function whose distribution is defined by γ parameters a, i.e., $r=f(u|a1, a2, \ldots, a\gamma)$. Then, the function f can be determined by finding the parameters $a1, a2, \ldots, a\gamma$ which minimize squared errors between the true values and the observed values. Specifically, the pixel value $r_m$ at each coordinate position of interest is calculated by determining the parameters of the function f such that the total sum of errors of the observed values at the observation points is minimized, according to the equation (3) below, to generate the regression curve (regression surface). It should be noted that, as shown by the equation (4) below, a weight $w_k$ may be set for each observation point $u_k$, and the regression curve (regression surface) may be generated by calculating the pixel value $r_m$ at each coordinate position of interest $u_m$ by the weighted least squares method.

$$r_m = \sum_k \{q_k - f(u_k)\}^2 \quad (3)$$

$$r_m = \sum_k w_k \{q_k - f(u_k)\}^2 \quad (4)$$

In the case where a moving average method is used, the regression surface is generated by calculating the pixel value at each coordinate position of interest by the moving average method. Specifically, considering the regression surface as a regression curve for ease of explanation, for the pixel value at each coordinate position of interest um, an average value $\{(qk-1)+qk+(qk+1)\}/3$ of the pixel values of the projection images Gi projected on three coordinate positions adjacent to the coordinate position of interest um, i.e., coordinate positions uk−1, uk, and uk+1, for example, is calculated, and the calculated average value is used as the pixel value at the coordinate position of interest um. It should be noted that a weight may be set for each pixel value. For example, weights may be set such that the weight is smaller as the distance from the coordinate position of interest um is greater.

In the case where regression using a kernel function is used, the regression curve (regression surface) is calculated by determining a kernel function, according to the equation (5) below, for each coordinate position of interest um and the observation point uk on the slice plane Tj on which the pixel values of the projection images are projected. The "argmin" in the equation (5) means that the value of r(um) that minimizes the right side is calculated.

$$r(u_m) = \arg\min_{r(u_{min})} \sum_k \{q_k - r(u_m)\}^2 K(u_k, u_m, q_k, q_m) \quad (5)$$

The above-described filtering for smoothing can be integrated into the regression analysis. In the case where the least squares method is used, using a low-dimensional function as the function f results in a higher level of smoothing of the generated regression surface. In contrast, using a high-dimensional function as the function f results in a higher level of sharpness of the generated regression surface. In the case where the moving average is used, the level of smoothing can be changed by changing the number of pixels for which the average is calculated, or changing the level of weighting. Namely, increasing the number of pixels for which the average is calculated results in a higher level of smoothing. Also, the level of smoothing may be changed by changing the level of weighting depending on the imaging conditions, as described above.

With the regression technique using a kernel function, the level of smoothing can be changed depending on the design of the kernel function. In particular, the regression technique using a kernel function allows obtaining an effect similar to that of the weighted least squares method and emphasizing edges depending on the design of the kernel function. For example, when the kernel function expressed by the equation (6) below is used, the regression surface is generated such that a pixel value closer to the observed value qk at the observation point uk is calculated when the distance between the coordinate position of interest um and the observation point uk is smaller. This allows obtaining a smoothing effect similar to that obtained by using a Gaussian filter. The "hx" in the equation (6) is a bandwidth parameter.

$$K(u_k, u_m) = \exp\left(\frac{-\|u_k - u_m\|^2}{h_x^2}\right) \quad (6)$$

Figure 8:
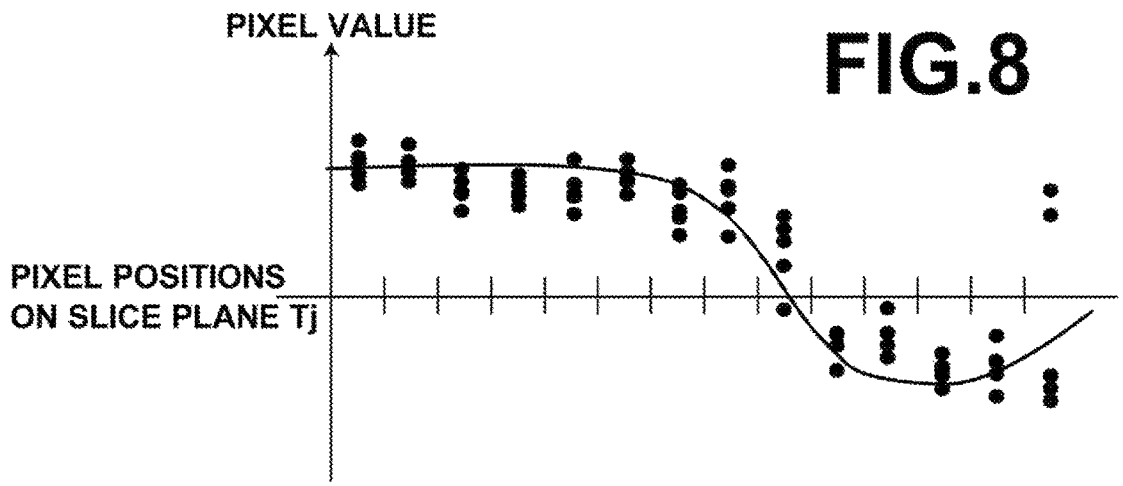
FIG. 8 is a diagram for explaining how a regression curve (regression surface) including outliers is generated.

In FIG. 7, two pixel values among the five pixel values projected on the rightmost pixel position on the slice plane Tj are largely different from the pixel values at the adjacent pixel positions. If there are pixel values that are largely different from the pixel values of the adjacent pixels, the value of the generated regression surface at the pixel position which includes the outliers is largely different from the value at the adjacent pixel position, as shown in FIG. 8. Then, when a tomographic image is generated from the calculated regression surface, as described later, the tomographic image includes an artifact at the pixel position corresponding to the outliers.

For this reason, the pixel value calculating unit 33 determines a pixel value which is largely different from the adjacent pixel values among the pixel values projected on the slice plane Tj as an outlier, and calculates the pixel value at each coordinate position of interest with removing the outlier pixel value. For example, the pixel value calculating unit 33 calculates a difference between each of the pixel values projected on the coordinate position of interest and an average value of pixel values at pixel positions adjacent to the coordinate position of interest on the slice plane Tj, and determines a pixel value whose difference from the average value exceeds a predetermined threshold value as an outlier to remove the outlier pixel value when the regression analysis is performed. In place of removing the outlier, the outlier pixel value may be weighted with a small weight.

Figure 9:
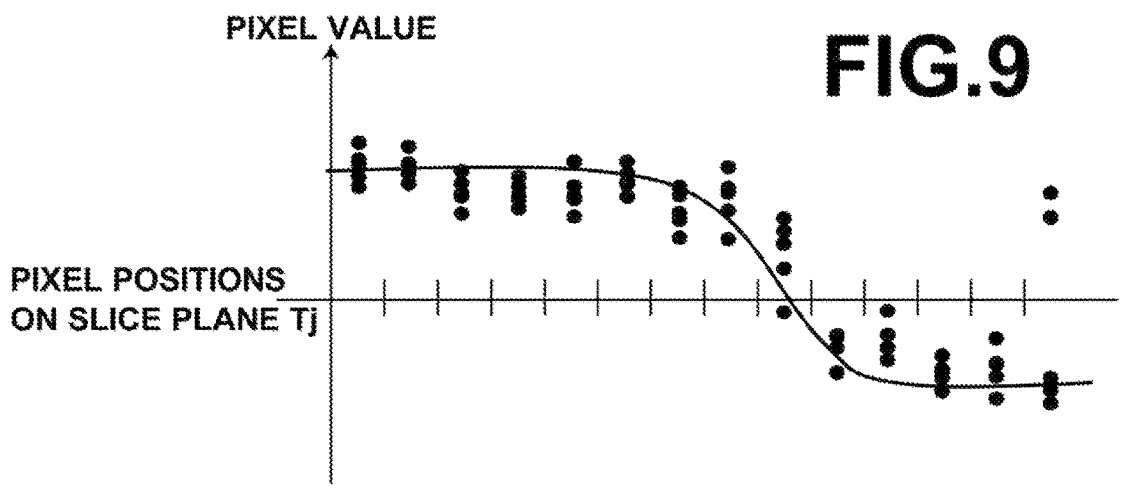
FIG. 9 is a diagram for explaining how a regression curve (regression surface) from which outliers are removed is generated.

When the regression curve (regression surface) is calculated with removing the outliers or weighting the outliers with a small weight, the value at the pixel position including the outliers does not differ largely from the value at the adjacent pixel position, as shown in FIG. 9. This allows preventing the tomographic image from including an artifact.

The operation to remove an outlier can be integrated into the regression analysis. In the case where the least squares method is used, the weighted least squares method shown by the equation (4) above may be used with weighting the outlier pixel values with 0 or a small weight. In the case where the moving average is used, a weighted average may be calculated with weighting the outlier pixel values with 0 or a small weight.

After the regression surface is generated, the pixel value calculating unit 33 samples the regression surface at a desired sampling interval to generate a tomographic image. The sampling interval may be stored in the storage 23 as a fixed value. The sampling interval may be changeable to an arbitrary value according to an instruction made via the input unit 4. For example, if the same sampling interval as that of the projection images is set, the tomographic image has the same resolution as that of the projection images Gi. If the sampling interval is set smaller than that of the projection images Gl, the tomographic image has a higher resolution than that of the projection images Gi. In contrast, if the sampling interval is set greater than that of the projection images Gi, the tomographic image has a lower resolution than that of the projection images Gi. In this case, the value of the sampling interval stored in the storage 23 is rewritten according to input by the operator via the input unit 4 and the sampling interval is changed. Alternatively, the sampling interval may be adjusted depending on the resolution of the display unit 3.

Figure 10:
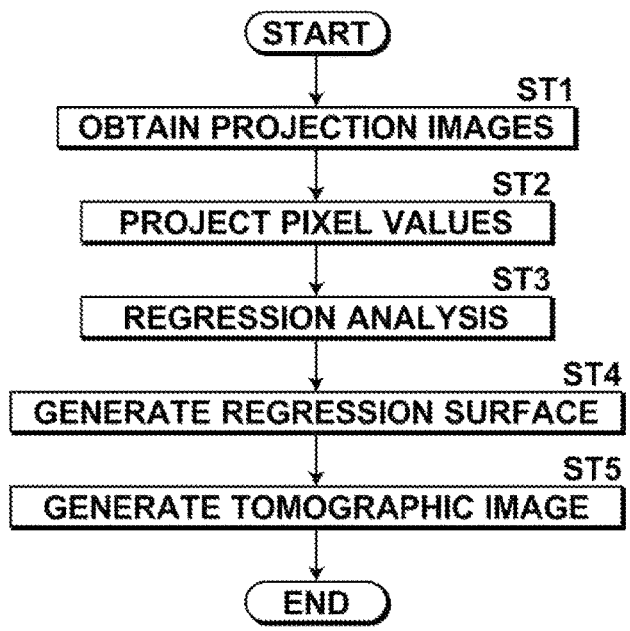
FIG. 10 is a flow chart illustrating a process performed in the first embodiment.

Next, a process performed in the first embodiment is described. FIG. 10 is a flow chart showing the process performed in the first embodiment. In response to an instruction to start the process made by the operator and received by the input unit 4, the tomosynthesis imaging is performed, and the image obtaining unit 31 obtains a plurality of projection images Gi (step ST1). Then, the pixel value projecting unit 32 projects pixel values of the projection images Gi on coordinate positions on a desired slice plane Tj of the breast M, while preserving the pixel values of the projection images obtained by the image obtaining unit 31 (step ST2).

Subsequently, the pixel value calculating unit 33 performs the regression analysis on the pixel values of the projection images Gi projected on the slice plane Tj (step ST3) to generate a regression surface that represents a tomographic image of the slice plane Tj (step ST4). Further, the pixel value calculating unit 33 samples the regression surface at a given sampling interval to generate a tomographic image (step ST5), and the process ends. It should be noted that, when another tomographic image at a different slice plane is to be generated, the operations in steps ST1 to ST5 are performed with changing the position of the slice plane.

As described above, in the first embodiment, pixel values of each of the projection images Gi are projected on coordinate positions on a desired slice plane Tj of the breast M, which is the subject, based on the positional relationship between the position of the x-ray source 16 with which each projection image Gi is taken and the radiation detector 15, while preserving the pixel values of the projection images Gi. Then, the pixel value at each coordinate position of interest is calculated by generating a regression surface by regression analysis, for example, based on the pixel values of the projection images Gi projected in a predetermined range on the slice plane Tj relative to the coordinate position of interest, to generate a tomographic image. When compared with the conventional techniques where only the pixel values of the projection images Gi projected on each coordinate position of interest are used to calculate the pixel value at the coordinate position of interest, this embodiment allows taking influence of pixel values around the coordinate position of interest into account, thereby reducing artifacts to allow generation of a tomographic image with even higher image quality. Further, since it is not necessary to repeat projecting the pixel values again and again, which is necessary in the iterative approximation reconstruction method, significant reduction of the calculation time can be achieved.

Further, a tomographic image with a desired resolution can be generated by calculating the pixel value at each coordinate position of interest by sampling the regression surface at a desired sampling interval.

Next, a second embodiment of the disclosure is described. It should be noted that the configuration of the tomographic image generation device according to the second embodiment is the same as the above-described configuration of the tomographic image generation device according to the first embodiment, and only the process performed is different. Therefore detailed description of the device is omitted in the following description. In the above-described first embodiment, pixel values of each of the projection images Gi at positions intersecting with the straight lines that connect the radiation source position and the individual pixel positions on the slice plane Tj, as shown in FIG. 5, are projected as pixel values at the pixel positions on the slice plane Tj on the straight lines. Whereas, in the second embodiment, for each of the different radiation source positions Si, pixel values at pixel positions on the corresponding projection image Gi on straight lines that connect the radiation source position Si and the individual pixel positions on the projection image Gi are projected on coordinate positions on the slice plane Tj intersecting with the straight lines.

FIG. 11 is a diagram for explaining how the pixel values are projected in the second embodiment. It should be noted that FIG. 11 explains a case where a projection image Gi obtained at a radiation source position Si is projected on a desired slice plane Tj (j=1 to m, where m is the number of slice planes) among slice planes of the breast M. As shown in FIG. 11, in the second embodiment, pixel values at pixel positions of the projection image Gi on the straight lines that connect the radiation source position Si and the individual pixel positions on the projection image Gi are projected as pixel values at coordinate positions on the slice plane Tj intersecting with the straight lines. The relationship among the coordinates (sxi, syi, szi) of the radiation source position at the radiation source position Si, the coordinates Tj(tx, ty, tz) of a pixel position on the slice plane Tj, and the coordinates (pxi, pyi) of a coordinate position Pi on the projection image Gi are as shown by the equations (1) above. Therefore the coordinate position on the slice plane Tj on which the pixel value at each pixel position on the projection image Gi is projected can be calculated by solving the equations (1) for tx and ty, where pxi and pyi in the equations (1) are the pixel position on the projection image Gi. In this manner, each pixel value of each projection image Gi is projected on the calculated coordinate position on the slice plane Tj.

In this case, as shown in FIG. 11, intersection points Tjx between the slice plane Tj and the straight lines that connect the radiation source position Si and the individual pixel positions on the projection image Gi may not be pixel positions on the slice plane Tj. In this case, in the second embodiment, the pixel values of the projection image Gi are projected on coordinate positions between the pixel positions on the slice plane Tj. This means that, in the second embodiment, the pixel values of the projection image are projected also on coordinate positions other than the pixel positions on the slice plane Tj.

Figure 12:
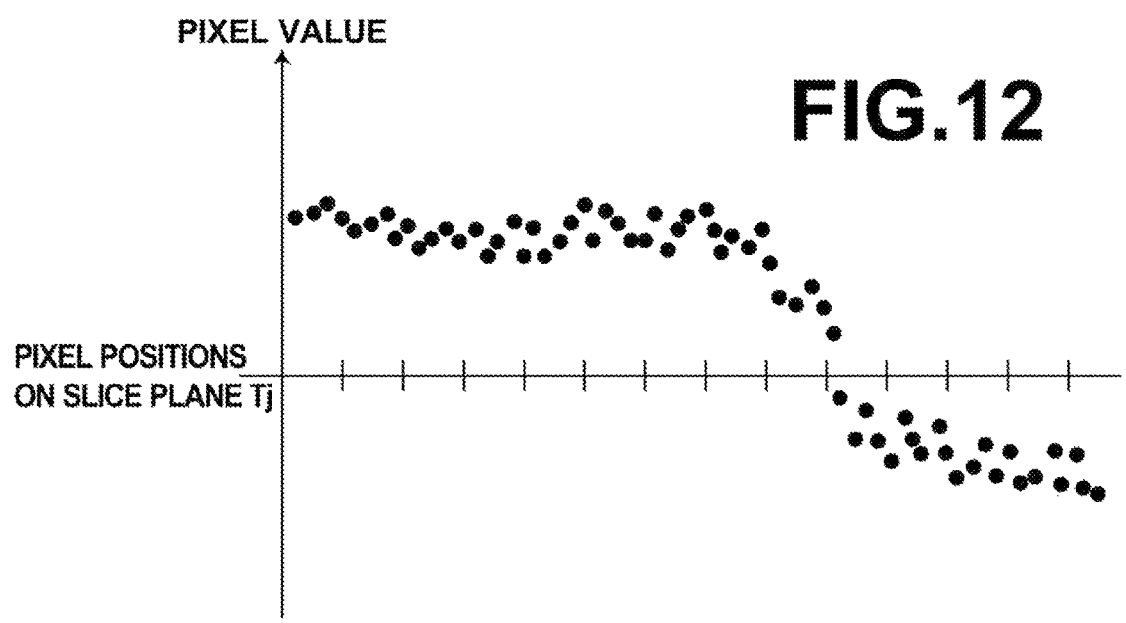
FIG. 12 is a diagram showing pixel values projected on a slice plane in the second embodiment.

In the second embodiment, the pixel value projecting unit 32 projects, for all the radiation source positions Si, the pixel values of all the projection images G1 to Gn on the slice plane Tj. Thus, pixel values corresponding to the number of pixels of all the projection images Gi are projected on coordinate positions including the pixel positions on the slice plane Tj, as shown in FIG. 12.

Similarly to the first embodiment, the pixel value calculating unit 33 in the second embodiment performs the filtering on the pixel values of the projection images Gi projected on the slice plane Tj, and performs the regression analysis to generate a regression surface. The filtering is performed with setting each coordinate position on the slice plane on which the pixel values are projected as the center.

In the second embodiment, since the pixel values of the projection images Gi are projected on coordinate positions on the slice plane Tj, as described above, it is not necessary to perform interpolation of the pixel values of the projection images Gi, which is necessary in the first embodiment. Compared with the first embodiment, image quality of the projection images is not degraded when they are projected. This allows achieving even higher image quality of the generated tomographic image.

Further, in the second embodiment, a spacing between the coordinate positions on the slice plane Tj on which the pixel value are projected is smaller than a spacing between the pixel positions on the slice plane Tj, and coordinate positions other than the pixel positions on the slice plane Tj also have pixel values. This allows generating a highly accurate regression surface based on the actually obtained pixel values of the projection images, even in a frequency band higher than the Nyquist frequency, which is determined by the spacing between the pixel positions on the slice plane Tj. Therefore, in the second embodiment, degradation of image quality can be suppressed even when a small sampling interval of the regression surface is set, thereby allowing generation of a tomographic image with even higher image quality.

Next, a third embodiment of the disclosure is described. It should be noted that the configuration of the tomographic image generation device according to the third embodiment is the same as the above-described configuration of the tomographic image generation device according to the first embodiment, and only the process performed is different. Therefore detailed description of the device is omitted in the following description. The difference between the third embodiment and the first embodiment lies in that, in the third embodiment, the image obtaining unit 31 further obtains a radiographic image by ordinary x-ray imaging, and the pixel value projecting unit 32 corrects projection positions on a slice plane Tj on which pixel values of the projection images are projected. It should be noted that the "ordinary x-ray imaging" as used herein refers to x-ray imaging where the x-ray source 16 is not moved and is fixed at a certain radiation source position, and the x-ray is applied to the subject under imaging conditions for obtaining a transmission image of the subject.

As shown in FIG. 13, the x-ray emitted from the x-ray source 16 is a cone beam, which spreads as it travels away from the x-ray source 16. The position of the surface of the radiation detector 15, at which the projection images Gi are obtained, is farther from the x-ray source 16 than the slice plane Tj. Therefore when the breast M is imaged with a certain radiation source position among different radiation source positions Si, the position of a structure BO, such as a mammary gland and a calcification, included in the breast M on the projection image Gi detected by the radiation detector 15 is different from the position of the structure BO in a tomographic image TGj of the slice plane Tj, as shown in FIG. 14.

When a radiographic image is obtained by the ordinary x-ray imaging, the position of the x-ray source 16 is fixed at a certain radiation source position, and the breast M is imaged under imaging conditions for obtaining a transmission image of the breast M. Therefore the geometrical positional relationship of the projection image obtained with the certain radiation source position is the same as that of the radiographic image. In this case, when the obtained radiographic image and the tomographic image are displayed side by side for diagnosis, the position of the structure BO in the radiographic image differs from the position of the structure 130 in the tomographic image. In the third embodiment, the pixel value projecting unit 32 corrects the coordinate position on the slice plane Tj on which the pixel value at each coordinate position of interest on the projection image Gi is projected based on the positional relationship between the radiation source position Si with which the projection image Gi is taken and the coordinate position of interest on the projection image Gi, such that the coordinate position of interest on the projection image Gi agrees with the coordinate position on the slice plane Tj on which the pixel value at the coordinate position of interest is projected.

Now, how the projection positions are corrected is described. As shown in FIG. 13, assuming that coordinates of the radiation source position at the radiation source position Si are (sxi, syi, szi), and coordinates of the structure BO on the slice plane Tj are Tj(tx, ty, tz), coordinates Pi(pxi, pyi) of the projection position on the radiation detector 15 on which the structure BO is projected are expressed by the equations (1) above.

Assuming that Pi is the coordinate position of interest, if the coordinate positions are not corrected, the coordinate position of interest Pi is projected on a coordinate position Tj on the slice plane Tj, and the coordinate position on the slice plane Tj on which the pixel value at the coordinate position of interest Pi is projected can be calculated by solving the equations (1) for tx and ty.

On the other hand, as shown in FIG. 13, when the x-ray source 16 is present on a line which is orthogonal to the detection surface of the radiation detector 15 and crosses the coordinate position Pi(pxi, pyi), the coordinate position of interest Pi is projected at the intersection point on the tomographic image of the slice plane Tj between the slice plane Tj and the straight line that connects the radiation source position Sc and the coordinate position Pi. In this case, the position of the structure BO on the tomographic image of the slice plane Tj is at the same two-dimensional coordinates as those on the projection image Gi taken with the radiation source position Sc, and the position of the structure BO on the projection image Gi agrees with the position of the structure BO on the tomographic image of the slice plane Tj. Therefore the coordinate position on the slice plane Tj on which the pixel value at the coordinate position of interest is projected is corrected by changing the radiation source position which serves as the reference when the pixel value of the projection image is projected on the slice plane Tj to the radiation source position Sc, which is present on the straight line that is orthogonal to the coordinate position of the pixel value to be projected on the projection image. Assuming that the coordinate position of the radiation source position Sc serving as the reference for the correction is (sxc, syc, szc), the relationship between the coordinate position of interest Pi and the coordinate position (tx,ty) on the slice plane Tj after the correction is expressed by the equation (7) below.

$$P_i(px_i, py_i) = \left( \frac{sz_i}{sz_i - tz} \frac{sz_c - tz}{sz_c} tx - \frac{tz}{sz_i - tz} sx_i + \frac{sz_i}{sz_i - tz} \frac{tz}{sz_c} sx_c, \right. \quad (7)$$
$$\left. \frac{sz_i}{sz_i - tz} \frac{sz_c - tz}{sz_c} ty - \frac{tz}{sz_i - tz} sy_i + \frac{sz_i}{sz_i - tz} \frac{tz}{sz_c} sy_c \right)$$

In the equation (7), $(sz_c-tz)/sz_c$ in the first term of the equation expressing each of pxi and pyi represents the enlargement factor at the coordinate position, and the third term represents the amount of shift of the coordinate position in the x direction or the y direction. Therefore the corrected coordinate position on the slice plane Tj on which the pixel value at the coordinate position of interest Pi is projected can be calculated by solving the equation (7) for tx and ty.

By correcting the coordinate positions on the slice plane Tj on which the pixel values of the projection images Gi are projected in this manner, the position of a structure, such as a tumor, included in the tomographic image can be made the same as the position of the corresponding structure included in the projection image, i.e., the radiographic image. This allows more accurate diagnosis using the radiographic image and the tomographic image.

Next, a fourth embodiment of the disclosure is described. FIG. 15 is a diagram illustrating the schematic configuration of a tomographic image generation device according to the fourth embodiment. It should be noted that the elements shown in FIG. 15 that are the same as those shown in FIG. 3 are denoted by the same reference numerals, and a detailed description thereof is omitted. The difference between the fourth embodiment and the first embodiment lies in that the tomographic image generation device according to the fourth embodiment includes a pseudo image generating unit 34 for generating a pseudo image from a plurality of tomographic images of a plurality of slice planes of the breast M.

The pseudo image generating unit 34 generates as the pseudo image an addition tomographic image by adding up corresponding pixel positions of a plurality of tomographic images TGj generated for a plurality of slice planes Tj. The thus generated addition tomographic image shows a pseudo transmission image of the subject, which appears as the same as a radiographic image obtained by the ordinary x-ray imaging. In this embodiment, the tomographic images have high image quality with reduced noise. By adding up such tomographic images, a high quality transmission image, i.e., a high quality pseudo radiographic image, can be generated.

In the fourth embodiment, when the pixel values of the projection images are projected on coordinate positions on each slice plane, the coordinate positions on the slice plane Tj are corrected similarly to the third embodiment to make the position of a corresponding structure the same among the tomographic images. This facilitates determining corresponding pixel values to perform the addition, thereby allowing generation of a radiographic image with even higher image quality.

It should be noted that, in place of an addition tomographic image, the pseudo image generating unit 34 may generate as the pseudo image a maximum projection image which is obtained by an MIP method that extracts maximum values from the corresponding pixel positions of the plurality of tomographic images. Alternatively, the pseudo image generating unit 34 may generate as the pseudo image a minimum projection image which is obtained by a minIP method that extracts minimum values from the plurality of tomographic images.

When the generated tomographic image is displayed on the display unit 3 in the above-described embodiments, an instruction to change the size of an area of interest on the tomographic image may be received to display an enlarged image of the area of interest for which the instruction to change the size is received. In this case, an area of the regression surface corresponding to the area of interest for which the instruction to change the size has been received is extracted, and a sampling interval which is smaller than the sampling interval of the tomographic image is set to sample the extracted area. This allows displaying an enlarged image A2 of the area of interest A1 specified on the tomographic image TGj, as shown in FIG. 16. The sampling interval here is preferably a sampling interval that is determined by the resolution of the display unit 3. While the enlarged image A2 shown in FIG. 16 is superimposed on the tomographic image TGj, the enlarged image A2 may be displayed in place of the tomographic image TGj, or the enlarged image A2 may be displayed side by side with the tomographic image TGj. In a case where an instruction to reduce an area of interest is made, a sampling interval that is greater than the sampling interval of the tomographic image is set to sample an extracted area of the regression surface corresponding to the area of interest.

Next, a fifth embodiment of the disclosure is described. FIG. 17 is a diagram illustrating the schematic configuration of a tomographic image generation device according to the fifth embodiment. It should be noted that the elements shown in FIG. 17 that are the same as those shown in FIG. 3 are denoted by the same reference numerals, and a detailed description thereof is omitted. The difference between the fifth embodiment and the first embodiment lies in that the tomographic image generation device according to the fifth embodiment includes a positional misalignment correcting unit 35 for correcting for positional misalignment between a plurality of slice plane projection images TGi, each slice plane projection image TGi being defined as an image formed by pixel values of each of the projection images Gi projected on the slice plane Tj.

When the tomosynthesis imaging is performed, it is difficult to accurately move the radiation source to the calculated radiation source positions, due to influence of a mechanical error, such as vibration during imaging or mechanical misalignment, and the radiation source positions during imaging may be different from the calculated radiation source positions. This positional error, or positional misalignment, hinders accurate alignment of the projection position of an object, resulting in degradation of the image quality of the tomographic image.

Further, when such tomosynthesis imaging is performed, a plurality of images of the subject are taken based on an instruction to start an imaging operation, and this imaging operation takes several seconds from the start to the end of the imaging operation, during which the subject may move. When there is such a body motion of the subject, it is difficult to accurately align the projection position of the object during the reconstruction, resulting in degradation of the image quality of the tomographic image.

Furthermore, the influence of a mechanical error and a body motion appears three-dimensionally and non-linearly in the subject, and it is difficult to remove the influence of a mechanical error and a body motion from the tomographic image by simply translating, rotating, and enlarging or reducing the projection images Gi by affine transformation, etc.

In the fifth embodiment, the positional misalignment correcting unit 35 corrects the positional misalignment between the slice plane projection images TGi. If there is no mechanical error and no body motion of the breast M during the imaging operation with moving the x-ray source 16 to different radiation source positions Si, the pixel values of the slice plane projection images TGi substantially agree with one another, as shown in FIG. 18. On the other hand, if there is a mechanical error or a body motion, a slice plane projection image corresponding to a projection image that is taken when the mechanical error or the body motion occurs has pixel positions that are shifted from the corresponding pixel positions of the other slice plane projection images, as shown in FIG. 19. The positional misalignment correcting unit 35 corrects the positional misalignment between the slice plane projection images TGi such that the positions of the slice plane projection images TGi agree with one another. Specifically, the positional misalignment correcting unit 35 detects feature points, such as an edge, an intersection point between edges, a corner of an edge, etc., included in each slice plane projection image TGi by using an algorithm such as SIFT (Scale-Invariant Feature Transform) or SURF (Speeded Up Robust Features), and transforms the slice plane projection images TGi such that the detected feature points agree among them, to thereby correct the positional misalignment. Thus, the positional misalignment between the slice plane projection images TGi is corrected, as shown in FIG. 18, and the distributions of pixel values of the slice plane projection images TGi substantially agree with one another.

It should be noted that the SIFT is a technique that describes feature quantities which are invariant to rotation and/or scaling of an image at feature points, and aligns the positions of a plurality of images based on the described feature quantities. The SURF is a technique for more quickly achieving the above-described alignment by substituting the operation performed in the SIFT with approximation. It should be noted that the operation to correct positional misalignment performed in this embodiment is not limited to the SIFT or SURF, and any other suitable technique may be used.

In the fifth embodiment, after the correction of the positional misalignment between the slice plane projection images TGi, the pixel value calculating unit 33 generates a tomographic image of the slice plane Tj by calculating the pixel values on the slice plane Tj, similarly to the above-described embodiments.

As described above, in the fifth embodiment, positional misalignment between the slice plane projection images TGi projected on the slice plane Tj is corrected. Thus, the influence of a three-dimensional mechanical error and a three-dimensional body motion can be handled only as a two-dimensional positional misalignment on the slice plane Tj. This allows effectively removing the positional misalignment due to a mechanical error and a body motion on the slice plane Tj, thereby improving the image quality of the tomographic image.

It should be noted that, in the tomographic images of adjacent slice planes, the corresponding pixel positions tend to have the same pixel value. For this reason, in the above-described embodiments, a plurality of regression surfaces at a plurality of slice planes of the breast M may be generated, and the regression surface of a slice plane of interest may be smoothed using the regression surfaces of the adjacent slice planes. Specifically, for a regression surface of a slice plane Tj, a correlation among pixel values at corresponding pixel positions on regression surfaces of three adjacent slice planes Tj−1, Tj, and Tj+1 is calculated. Then, if the correlation exceeds a predetermined threshold value, smoothing is performed for the pixel position on the slice plane Tj by calculating an average of the pixel values of the three slice planes Tj−1, Tj, and Tj+1, for example. As the correlation, absolute difference values between the pixel values at the corresponding pixel positions can be used, for example. This allows taking the influence of pixel values at adjacent slice planes into account, thereby allowing generation of a high image quality tomographic image with even reduced noise.

Further, after the regression surface is generated in the above-described embodiments, the regression surface may be modified by calculating an absolute difference value between each pixel value projected on each coordinate position on the slice plane Tj and the value of the regression surface at the corresponding coordinate position, determining a pixel value whose absolute difference value exceeds a predetermined threshold value as an outlier, and removing the outlier or weighting the outlier with a small weight. For example, in the case where the regression curve as shown in FIG. 8 is generated, an absolute difference value between each of the five pixel values projected on the rightmost pixel position on the slice plane Tj and the value of the regression curve at the corresponding pixel position is calculated. In this case, the absolute difference values of the two pixel values having the large values exceed the threshold value. Then, the two pixels having the large values are removed as outliers or weighted with a small weight to modify the regression curve. This allows generating a regression curve, as shown in FIG. 9, where the value at the pixel position including the outliers does not largely differ from the value at the adjacent pixel position.

Further, while the regression surface is generated after all the pixel values of the projection images Gi are projected on the slice plane Tj in the above-described embodiments, the regression surface may be generated for each projection image Gi. In this case, a correlation at corresponding coordinate positions among the regression surfaces calculated for the individual projection images Gi is calculated. As the correlation, absolute difference values can be used. Then, if there is a regression surface having a small correlation, i.e., having a pixel value whose absolute difference value exceeds a predetermined threshold value, the pixel value of the regression surface at the coordinate position with the small correlation is determined as an outlier and is removed or weighted with a small weight, and then a regression surface is generated based on pixel values of all the projection images Gi projected on coordinate positions on the slice plane Tj.

When the tomosynthesis imaging is performed, the amount of x-ray reaching the radiation detector 15 varies between when the x-ray orthogonally enters the radiation detector 15 and when the x-ray obliquely enters the radiation detector 15, and the image quality of the projection images Gi varies depending on the radiation source position with which each projection image Gi is taken. Specifically, comparing a projection image that is obtained when the x-ray orthogonally enters the radiation detector 15 with a projection image that is obtained when the x-ray obliquely enters the radiation detector 15, the latter has a lower density and thus is whiter due to a smaller amount of radiation reaching the radiation detector 15. Further, there may be density irregularity among the projection images due to influence of characteristics of the radiographic imaging apparatus, etc. It is therefore preferred to project the pixel values of the projection images Gi on coordinate positions on the slice plane Tj after the variation of image quality and the density irregularity among the projection images Gi are corrected.

The variation of density based on the amount of radiation reaching the detector and the density irregularity are included in low frequency components of the projection images Gi. It should be noted that the low frequency refers to frequencies that are appropriately set to be 50% or less of the Nyquist frequency, which is determined by the spacing between the pixel positions of the projection images Gi. It is therefore preferred to remove the low frequency components from the projection images Gi and project the pixel values of the projection images Gi from which the low frequency components are removed on coordinate positions on the slice plane Tj. This allows correcting the variation of image quality among the projection images Gi, thereby allowing generation of a tomographic image with even higher image quality. The removal of the low frequency components can be achieved by performing frequency decomposition on the projection images, for example, to calculate the low frequency components, and subtract the calculated low frequency components from the projection images. Alternatively, the removal of the low frequency components may be achieved by generating a blurred image of each projection image, and subtracting the blurred image from the projection image.

Further, in the above-described embodiments, the process to generate the regression surface may be sequentially iterated. For example, in the above-described method for calculating the regression surface using the weighted least squares method, after the regression surface is generated, the weight wk for each observation point uk is calculated according to the equation (8) below, where f(uk) is the value of the calculated regression curve at the observation point uk:

$$wk = e^{-(qk-f(uk))^2} \qquad (8)$$

According to the equation (8), a smaller value of the weight k is calculated for a larger difference between each observed value qk and the value of the regression curve at the observation point uk. Then, when a regression curve is generated according to the equation (4) above using the thus calculated weights wk, influence of values that are largely different from the previously generated regression curve is reduced in the newly generated regression curve. In particular, if there are outliers, the outliers are weighted with smaller weights, thereby reducing artifacts at pixel positions of the outliers in a generated tomographic image. It should be noted that the number of iterations of the process to generate the regression surface may be set in advance, or the process to generate the regression surface may be iterated until a predetermined convergence condition is satisfied. The convergence condition may, for example, be that the difference, i.e., the value of qk−f(uk), resulting from the iterative calculation is not greater than a threshold value.

It should be noted that the process to generate the regression surface may be sequentially iterated also in the case where the regression curve is generated using the moving average method or using a kernel function. In the case where the moving average method is used, the weight for each observation point uk may be calculated similarly to the equation (8) above, and calculation of the weighted moving average may be iterated. In the case where the technique using a kernel function is used, a term for calculating the weight wk, as shown by the equation (8), may be combined into the equation for determining the kernel function, and the regression curve may be generated by iterating the technique using the kernel function.

While the tomographic image is generated by generating the regression surface by the pixel value calculating unit 33 in the above-described embodiments, the tomographic image may be generated by calculating the pixel values at the pixel positions on the slice plane Tj by regression analysis, without generating a regression surface. In this case, the sampling interval of the tomographic image to be generated is set in advance, and each coordinate position corresponding to the sampling interval is set as the pixel position of interest on the slice plane Tj to calculate the pixel value at the pixel position of interest by the regression analysis.

Further, while the subject of the tomosynthesis imaging in the above-described embodiments is the breast M, the disclosure is also applicable to tomosynthesis imaging with a subject other than a breast.

While only the x-ray source 16 is moved in the above-described embodiments, some imaging apparatuses allow moving the x-ray source 16 and the radiation detector 15 synchronously with each other. In this case, the x-ray source 16 and the radiation detector 15 may be moved synchronously with each other. Alternatively, the x-ray source 16 may be fixed and only the radiation detector 15 may be moved.

While the disclosure is applied to an imaging apparatus that performs tomosynthesis imaging in the above-described embodiments, the disclosure is applicable to any imaging apparatus that obtains a plurality of projection images by imaging a subject with different radiation source positions. For example, the disclosure is applicable to a CT imaging apparatus, where the radiation source and the radiation detector are disposed to face each other with the subject being the center, and the set of the radiation source and the radiation detector is rotated around the subject to obtain a plurality of projection images while applying radiation from different angles.

While the trajectory of the x-ray source 16 is a circular arc in the above-described embodiments, the trajectory of the x-ray source 16 may be a straight line.

Now, advantageous effects of the embodiments of the disclosure are described.

In the case where, for each of the different radiation source positions, pixel values at pixel positions on the corresponding projection image on straight lines that connect the radiation source and the individual pixel positions on the projection image are projected as pixel values at coordinate positions on the slice plane at which the slice plane intersects with the straight lines, it is not necessary to perform interpolation of the pixel values when the pixel values are projected. This allows generating a tomographic image with even higher image quality. In particular, since the pixel values are also projected on coordinate positions on the slice plane that are different from coordinate positions corresponding to pixel positions of the tomographic image, a high resolution and high image quality tomographic image can be generated.

In the case where the pixel values at the pixel positions on the slice plane are calculated by performing the regression analysis to generate a regression surface that represents a tomographic image of the slice plane, and sampling the regression surface at a desired sampling interval, a tomographic image with a desired resolution can be generated.

Further, when the regression analysis is performed, changing the sharpness of the pixel value at the coordinate position of interest allows emphasizing the sharpness of the pixel value at the coordinate position of interest or reducing the sharpness to achieve smoothing to suppress noise. This allows generating a tomographic image having a desired image quality.

In the case where the level of change of the sharpness is changed depending on information about at least one of the imaging conditions under which the projection images are taken and a structure of the subject included in the projection images, a tomographic image having a desired image quality depending on at least one of the imaging conditions and the structure of the subject can be generated.

In the case where the pixel value at the coordinate position of interest is calculated with removing an outlier pixel value among pixel values of the projection images projected in a predetermined range relative to the coordinate position of interest or weighting the outlier pixel value with a small weight, influence of the pixel value which is highly possible to be an artifact can be reduced, thereby allowing generation of a tomographic image with even higher image quality.

It should be noted that the difference of the radiation source position may cause low frequency irregularity among the projection images. In this case, influence of the low frequency irregularity can be reduced by removing the low frequency components of the projection images, and projecting pixel values of the projection images from which the low frequency components are removed on coordinate positions on the slice plane, thereby allowing generation of a tomographic image with even higher image quality.

The radiation emitted from the radiation source is a cone beam, which spreads as it travels away from the radiation source. Since the position of the surface of the detecting unit, at which the projection images are obtained, is farther from the radiation source than the slice plane, the two-dimensional coordinate position of a structure included in the subject in each projection image differs from the position of the structure in the tomographic image of the slice plane.

In this case, the two-dimensional coordinate position of the structure included in the subject in the tomographic image can be made agree with the two-dimensional coordinate position of the structure in the projection image obtained with a certain radiation source position by correcting the coordinate position on the slice plane on which the pixel value at each coordinate position of interest is projected based on the positional relationship between the certain radiation source position and the coordinate position of interest, such that the two-dimensional coordinates of the coordinate position of interest on the projection image obtained with the certain radiation source position agrees with the two-dimensional coordinates of the coordinate position on the slice plane on which the pixel value at the coordinate position of interest is projected, and projecting the pixel values of the projection images on the corrected coordinate positions on the slice plane.

In this case, when a radiographic image is obtained by imaging the subject with the certain radiation source position, a tomographic image is generated by calculating the pixel value at each coordinate position of interest on the slice plane with the pixel values of the projection images being projected on the corrected coordinate positions, and the radiographic image and the tomographic image are displayed, the two-dimensional coordinate position of a structure included in the subject in the displayed radiographic image agrees with the two-dimensional coordinate position of the structure in the displayed tomographic image. This allows more appropriate diagnosis.

In the case where a plurality of tomographic images at a plurality of slice planes of the subject are generated, and an addition tomographic image is generated by adding up the tomographic images, a pseudo transmission image having even higher image quality can be generated.

What is claimed is:

1. A tomographic image generation device comprising:
an image obtaining unit for obtaining a plurality of projection images corresponding to different radiation source positions, the projection images being taken by moving a radiation source relative to a detecting unit and applying radiation to a subject from the different radiation source positions to which the radiation source is moved;
a pixel value projecting unit for projecting pixel values of the projection images on coordinate positions on a desired slice plane of the subject based on a positional relationship between the radiation source position with which each of the projection images is taken and the detecting unit, while preserving the pixel values of the projection images; and
a pixel value calculating unit for calculating a pixel value at each coordinate position of interest on the slice plane based on a plurality of pixel values of the projection images projected in a predetermined range relative to the coordinate position of interest on the slice plane to thereby generate a tomographic image of the slice plane;
wherein the pixel value projecting unit projects, for each of the different radiation source positions, pixel values at coordinate positions on the corresponding projection image intersecting with straight lines that connect the radiation source position and individual pixel positions on the slice plane as pixel values at the pixel positions on the slice plane on the straight lines, and
wherein the pixel value calculating unit calculates the pixel value at the coordinate position of interest by performing regression analysis on pixel values of the projection images projected on the slice plane.

2. The tomographic image generation device as claimed in claim 1, wherein the pixel value projecting unit projects, for each of the different radiation source positions, pixel values at pixel positions on the corresponding projection image on straight lines that connect the radiation source position and the individual pixel positions on the projection image as pixel values at coordinate positions on the slice plane intersecting with the straight lines.

3. The tomographic image generation device as claimed in claim 2, wherein a spacing between coordinate positions on the slice plane is smaller than a spacing between pixel positions on the slice plane.

4. The tomographic image generation device as claimed in claim 1, wherein the pixel value calculating unit calculates pixel values at pixel positions on the slice plane by performing the regression analysis to generate a regression surface that represents a tomographic image of the slice plane, and sampling the regression surface at a desired sampling interval, to thereby generate the tomographic image.

5. The tomographic image generation device as claimed in claim 4, wherein the sampling interval is different from a sampling interval of the projection images.

6. The tomographic image generation device as claimed in claim 4, wherein, if an instruction to change the size of an area of interest in the tomographic image being displayed is received, the pixel value calculating unit generates a tomographic image of the area of interest with changing the sampling interval of an area of the regression surface corresponding to the area of interest according to the instruction to change.

7. The tomographic image generation device as claimed in claim 1, wherein the pixel value calculating unit changes sharpness of the pixel value at the coordinate position of interest when the regression analysis is performed.

8. The tomographic image generation device as claimed in claim 7, wherein the pixel value calculating unit changes a level of change of the sharpness depending on information of at least one of imaging conditions under which the projection images are taken and a structure of the subject included in the projection images.

9. The tomographic image generation device as claimed in claim 1, wherein the pixel value calculating unit calculates the pixel value at the coordinate position of interest with removing an outlier pixel value among the pixel values of the projection images projected in the predetermined range relative to the coordinate position of interest or weighting the outlier pixel value with a small weight.

10. The tomographic image generation device as claimed in claim 1, wherein the pixel value projecting unit removes low frequency components of the projection images, and projects pixel values of the projection images from which the low frequency components are removed on coordinate positions on the slice plane.

11. The tomographic image generation device as claimed in claim 1, wherein the pixel value projecting unit corrects, based on a positional relationship between a certain radiation source position and each coordinate position of interest on the projection image corresponding to the certain radiation source position, a coordinate position on the slice plane on which a pixel value at the coordinate position of interest on the projection image is projected such that two-dimensional coordinates of the coordinate position of interest on the projection image agrees with two-dimensional coordinates of the coordinate position on the slice plane on which the pixel value at the coordinate position of interest on the projection image is projected, and projects the pixel values of the projection images on the corrected coordinate positions on the slice plane.

12. The tomographic image generation device as claimed in claim 11, wherein the image obtaining unit obtains a radiographic image of the subject taken by applying the radiation to the subject from the certain radiation source position,
the pixel value calculating unit generates the tomographic image by calculating the pixel value at the coordinate position of interest on the slice plane with the pixel values of the projection images being projected on the corrected coordinate positions, and
the tomographic image generation device further comprises a display unit for displaying the radiographic image and the tomographic image.

13. The tomographic image generation device as claimed in claim 1, wherein the pixel value projecting unit and the pixel value calculating unit generate the tomographic image for each of a plurality of slice planes of the subject, and
the tomographic image generation device further comprises a pseudo image generating unit for generating a pseudo image from the tomographic images.

14. The tomographic image generation device as claimed in claim 1, wherein the pixel value calculating unit calculates weighting factors based on a difference between the pixel value at the coordinate position of interest and a pixel value at a coordinate position of each projection image corresponding to the coordinate position of interest, and calculates the pixel value at the coordinate position of interest again based on the plurality of pixel values of the projection images and the weighting factors to calculate a new pixel value at the coordinate position of interest.

15. The tomographic image generation device as claimed in claim 14, wherein the pixel value calculating unit iterates calculating new weighting factors using the new pixel value at the coordinate position of interest, and calculating a new pixel value at the coordinate position of interest again based on the plurality of pixel values of the projection images and the new weighting factors.

16. A tomographic image generation method comprising the steps of:
obtaining a plurality of projection images corresponding to different radiation source positions, the projection images being taken by moving a radiation source relative to a detecting unit and applying radiation to a subject from the different radiation source positions to which the radiation source is moved;
projecting pixel values of the projection images on coordinate positions on a desired slice plane of the subject based on a positional relationship between the radiation source position with which each of the projection images is taken and the detecting unit, while preserving the pixel values of the projection images; and
calculating a pixel value at each coordinate position of interest on the slice plane based on a plurality of pixel values of the projection images projected in a predetermined range relative to the coordinate position of interest on the slice plane to thereby generate a tomographic image of the slice plane;
wherein, for each of the different radiation source positions, pixel values are projected at coordinate positions on the corresponding projection image intersecting with straight lines that connect the radiation source position and individual pixel positions on the slice plane as pixel values at the pixel positions on the slice plane on the straight lines, and
wherein the pixel value is calculated at the coordinate position of interest by performing regression analysis on pixel values of the projection images projected on the slice plane.

17. A non-transitory recording medium containing a tomographic image generation program for causing a computer to execute the steps of:
obtaining a plurality of projection images corresponding to different radiation source positions, the projection images being taken by moving a radiation source relative to a detecting unit and applying radiation to a subject from the different radiation source positions to which the radiation source is moved;
projecting pixel values of the projection images on coordinate positions on a desired slice plane of the subject based on a positional relationship between the radiation source position with which each of the projection images is taken and the detecting unit, while preserving the pixel values of the projection images; and
calculating a pixel value at each coordinate position of interest on the slice plane based on a plurality of pixel values of the projection images projected in a predetermined range relative to the coordinate position of interest on the slice plane to thereby generate a tomographic image of the slice plane;
wherein, for each of the different radiation source positions, pixel values are projected at coordinate positions on the corresponding projection image intersecting with straight lines that connect the radiation source position and individual pixel positions on the slice plane as pixel values at the pixel positions on the slice plane on the straight lines, and
wherein the pixel value is calculated at the coordinate position of interest by performing regression analysis on pixel values of the projection images projected on the slice plane.

18. A tomographic image generation device comprising:
an image obtaining unit for obtaining a plurality of projection images corresponding to different radiation source positions, the projection images being taken by moving a radiation source relative to a detecting unit and applying radiation to a subject from the different radiation source positions to which the radiation source is moved;
a pixel value projecting unit for projecting pixel values of the projection images on coordinate positions on a desired slice plane of the subject based on a positional relationship between the radiation source position with which each of the projection images is taken and the detecting unit, while preserving the pixel values of the projection images; and a pixel value calculating unit for calculating a pixel value at each coordinate position of interest on the slice plane based on a plurality of pixel values of the projection images projected in a predetermined range relative to the coordinate position of interest on the slice plane to thereby generate a tomographic image of the slice plane, wherein the pixel value projecting unit projects, for each of the different radiation source positions, pixel values at pixel positions on the corresponding projection image on straight lines that connect the radiation source position and the individual pixel positions on the projection image as pixel values at coordinate positions on the slice plane intersecting with the straight lines, and wherein the pixel value calculating unit calculates the pixel value at the coordinate position of interest by performing regression analysis on pixel values of the projection images projected on the slice plane.

19. A tomographic image generation method comprising the steps of:

obtaining a plurality of projection images corresponding to different radiation source positions, the projection images being taken by moving a radiation source relative to a detecting unit and applying radiation to a subject from the different radiation source positions to which the radiation source is moved;

projecting pixel values of the projection images on coordinate positions on a desired slice plane of the subject based on a positional relationship between the radiation source position with which each of the projection images is taken and the detecting unit, while preserving the pixel values of the projection images; and calculating a pixel value at each coordinate position of interest on the slice plane based on a plurality of pixel values of the projection images projected in a predetermined range relative to the coordinate position of interest on the slice plane to thereby generate a tomographic image of the slice plane, wherein, for each of the different radiation source positions, pixel values are projected at pixel positions on the corresponding projection image on straight lines that connect the radiation source position and the individual pixel positions on the projection image as pixel values at coordinate positions on the slice plane intersecting with the straight lines, and wherein the pixel value is calculated at the coordinate position of interest by performing regression analysis on pixel values of the projection images projected on the slice plane.

20. A non-transitory recording medium containing a tomographic image generation program for causing a computer to execute the steps of:

obtaining a plurality of projection images corresponding to different radiation source positions, the projection images being taken by moving a radiation source relative to a detecting unit and applying radiation to a subject from the different radiation source positions to which the radiation source is moved;

projecting pixel values of the projection images on coordinate positions on a desired slice plane of the subject based on a positional relationship between the radiation source position with which each of the projection images is taken and the detecting unit, while preserving the pixel values of the projection images; and calculating a pixel value at each coordinate position of interest on the slice plane based on a plurality of pixel values of the projection images projected in a predetermined range relative to the coordinate position of interest on the slice plane to thereby generate a tomographic image of the slice plane, wherein, for each of the different radiation source positions, pixel values are projected at pixel positions on the corresponding projection image on straight lines that connect the radiation source position and the individual pixel positions on the projection image as pixel values at coordinate positions on the slice plane intersecting with the straight lines, and wherein the pixel value is calculated at the coordinate position of interest by performing regression analysis on pixel values of the projection images projected on the slice plane.

* * * * *